(12) United States Patent
Hoefle et al.

(10) Patent No.: US 7,754,885 B2
(45) Date of Patent: Jul. 13, 2010

(54) TUBULYSINS, METHOD FOR PRODUCING THE SAME AND TUBULYSIN PREPARATIONS

(75) Inventors: Gerhard Hoefle, Braunschweig (DE); Nicole Glaser, Braunschweig (DE); Heinrich Steinmetz, Braunschweig (DE); Thomas Leibold, Braunschweig (DE); Florenz Sasse, Braunschweig (DE)

(73) Assignee: Helmholtz-Zentrum fuer Infektionsforschung GmbH, Braunschweig (DE)

( * ) Notice: Subject to any disclaimer, the term of this patent is extended or adjusted under 35 U.S.C. 154(b) by 1083 days.

(21) Appl. No.: 10/535,630

(22) PCT Filed: Oct. 20, 2003

(86) PCT No.: PCT/EP03/11603

§ 371 (c)(1), (2), (4) Date: Nov. 4, 2005

(87) PCT Pub. No.: WO2004/046170

PCT Pub. Date: Jun. 3, 2004

(65) Prior Publication Data

US 2006/0128754 A1    Jun. 15, 2006

(30) Foreign Application Priority Data

Nov. 21, 2002   (DE) ................................ 102 54 439

(51) Int. Cl.
*C07D 417/00* (2006.01)
*A61K 31/445* (2006.01)

(52) U.S. Cl. ...................................... 546/208; 514/326

(58) Field of Classification Search ................ 546/208; 514/326

See application file for complete search history.

(56) References Cited

FOREIGN PATENT DOCUMENTS

| DE | 196 38 870 A | 3/1998 |
|----|---|---|
| DE | 100 08 089 A | 10/2001 |

OTHER PUBLICATIONS

Wolff et al Burger's Medicinal Chemistry and Drug Discovery, 5th Edition, vol. 1: Principles and Practice 1995, 974-977.*
Hawley's Condensed Chemical Dictionary, 14th Ed., John Wiley & Sons, Inc. 2001, New York.*
Hamel E. et al.: "Antimitotic Peptides and Depsipeptides" *Current Medicinal Chemistry, Anti-Cancer Agents*, Bentham Science Publishers, Hilversum, NL, vol. 2, No. 1, Jan. 2002, pp. 19-53.
Sasse F. et al.: "Tubulysins, New Cytostatic Peptides from Myxobacteria Acting on Microtubuli Production, Isolation, Physico-Chemical and Biological Properties" *Journal of Antibiotics, Japan Antibiotics Research Association*, Tokyo, JP, vol. 53, No. 9, Sep. 2000 pp. 879-885.

* cited by examiner

Primary Examiner—Rita J Desai
Assistant Examiner—John Mabry
(74) Attorney, Agent, or Firm—Frommer Lawrence & Haug LLP; Ronald R. Santucci

(57) ABSTRACT

The invention relates to a compound of the following general formula (tubulysin)

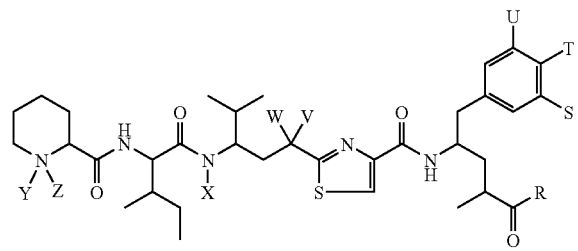

having the following meanings for R, $R^1$, $R^2$, $R^3$, $R^4$, $R^5$, $R^6$, $R^7$, $R^8$, $R^9$, $R^{10}$, $R^{11}$, S, T, U, V, W, X, Y and Z:

R=H, alkyl, aryl, OR1, NR1R2 or

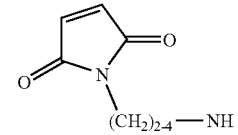

$R^1$=H, $C_{1-6}$alkyl or aryl
$R^2$=H, $C_{1-6}$alkyl or aryl
S=H, Hal, $NO_2$ or $NHR^3$
U=H, Hal, $NO_2$ or $NHR^3$
$R^3$=H, HCO or $C_{1-4}$alkyl-CO
T=H or $OR^4$
$R^4$=H, $C_{1-4}$alkyl, aryl, $COR^5$, $P(O)(OR^6)_2$ or $SO_3R^6$
$R^5$=$C_{1-6}$alkyl, alkenyl, aryl or heteroaryl
$R^6$=H, alkyl or a metal ion
V=H, $OR^7$, Hal or (for W=O) O
$R^7$=H, $C_{1-4}$alkyl or $COR^8$
R5=$C_{1-4}$alkyl, alkenyl or aryl
W=H or $C_{1-4}$alkyl or (for V=O) O
X=H, $C_{1-4}$alkyl, alkenyl or $CH_2OR^9$
$R^9$=H, $C_{1-4}$alkyl, alkenyl, aryl or $COR^{10}$
$R^{10}$=$C_{1-6}$alkyl, alkenyl, aryl or heteroaryl
Y=(for Z=$CH_3$ or $COR^{11}$) free electron pair or (for Z=$CH_3$)O
$R^{11}$=$C_{1-4}$alkyl, $CF_3$ or aryl and/or
Z=(for Y=O or free electron pair) $CH_3$ or (for Y=free electron pair) $COR^{11}$.

16 Claims, 9 Drawing Sheets a) 0.1 M HCl, dioxane, 50°C; b) 0.1 M HCl, 100°C; c) NH₃, MeOH; d) 1 M NaOH, MeOH; e) 0.5 M HCl, 100°C 12  T = H, OCOR⁵
    $R^{10}$ = $C_1$-$C_6$alkyl, $C_1$-$C_6$alkenyl, aryl, heteroaryl 13  T = H, OH
    $R^{10}$ = $C_1$-$C_6$alkyl, $C_1$-$C_6$alkenyl, aryl, heteroaryl a) $R^{10}$COCl, Et$_3$N; b) NH$_3$

1-6   T = H, OH
R¹⁰ = C₁-C₆alkyl a)

14   R⁹ = C₁-C₄alkyl, alkenyl, aryl a) *p*-CH₃-C₆H₄SO₂OH, R⁹OH, THF, 80°C

T = H, OH
R⁷ = H, COCH₃ a) NaCNBH$_3$, TFA, MeOH; b) NaCNBH$_3$, Me$_3$SiCl, CH$_3$CN a) EDC, R¹OH, DMAP, CH₂Cl₂; b) EDC, RH, CH₂Cl₂ or isobutyl chloroformate, Et₃N, RH, abs. THF
c) RLi; d) EDC, 1-(2-aminoethyl)-pyrrole-2,5-dione, CH₂Cl₂ a) P(O)(OR⁶)₂OH, I₂, pyridine, CH₂Cl₂ or pyridine-SO₃; b) R⁵COCl, Et₃N, abs. THF;
c) Ag₂O, R⁴I, CH₂Cl₂; for R⁴ = CH₃: CH₂N₂, MeOH; d) pig liver esterase, KH₂PO₄ buffer, 36°C;

a) $C_5Cl_5NF$ triflate, $SO_2Cl_2$, NBS, ICl; b) $NaNO_2$, $CH_3COOH$, EtOH; c) Pd/C, $H_2$, EtOH; d) $(R^3CO)_2O$ a) m-CPBA, CH$_2$Cl$_2$; b) Ac$_2$O, 75°C

TUBULYSINS, METHOD FOR PRODUCING THE SAME AND TUBULYSIN PREPARATIONS

This is a 371 filing of PCT/EP2003/011603 filed Oct. 20, 2003, published on Jun. 3, 2004 under publication number WO 2004/046170 A and claims priority benefits from German Patent Application No. DE 102 54 439.5 filed Nov. 21, 2002.

Tubulysins are known as compounds of the following general formula; cf., for example, F. Sasse, H. Steinmetz, J. Heil, G. Höfle, H. Reichenbach, *J. Antibiot.* 2000, 53, 579-558, and H. Reichenbach, G. Höfle, F. Sasse, H. Steinmetz (GBF), DE 196 38 870 A1, 1996.

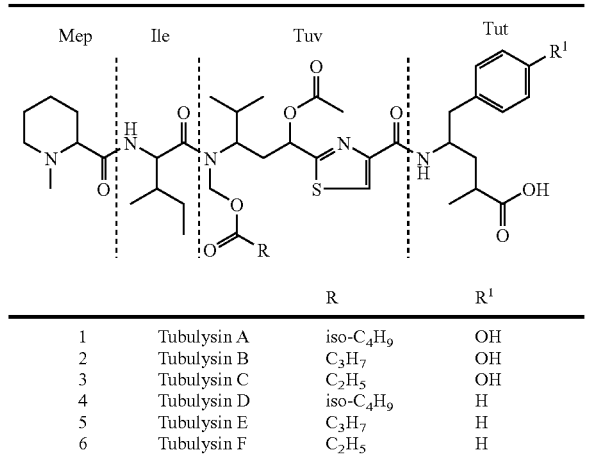

|   |           | R          | $R^1$ |
|---|-----------|------------|-------|
| 1 | Tubulysin A | iso-$C_4H_9$ | OH |
| 2 | Tubulysin B | $C_3H_7$   | OH |
| 3 | Tubulysin C | $C_2H_5$   | OH |
| 4 | Tubulysin D | iso-$C_4H_9$ | H |
| 5 | Tubulysin E | $C_3H_7$   | H |
| 6 | Tubulysin F | $C_2H_5$   | H |

The problem of the invention is to make available new tubulysins, processes for the preparation thereof and preparations comprising tubulysins, especially as cytostatic agents.

An embodiment of the invention relates to a compound of the following general formula I (tubulysin):

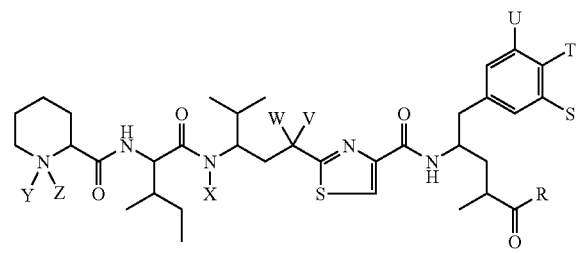

R, $R^1$, $R^2$, $R^3$, $R^4$, $R^5$, $R^6$, $R^7$, $R^8$, $R^9$, $R^{10}$, $R^{11}$, S, T, U, V, W, X, Y and Z having the following meanings:

R=H, alkyl, aryl, OR1, NR1R2 or

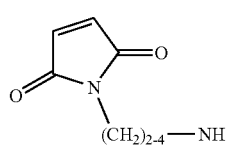

$R^1$=H, alkyl or aryl $R^2$=H, alkyl or aryl

S=H, Hal, $NO_2$ or $NHR^3$

U=H, Hal, $NO_2$ or $NHR^3$ $R^3$=H, HCO or $C_{1-4}$alkyl-CO

T=H or $OR^4$ $R^4$=H, alkyl, aryl, $COR^5$, $P(O)(OR^6)_2$ or $SO_3R^6$ $R^5$=alkyl, alkenyl, aryl or heteroaryl $R^6$=H, alkyl or a metal ion V=H, $OR^7$, Hal or (with W) O $R^7$=H, alkyl or $COR^8$ $R^8$=alkyl, alkenyl or aryl W=H or alkyl or (with V) O X=H, alkyl, alkenyl or $CH_2OR^9$ $R^9$=H, alkyl, alkenyl, aryl or $COR^{10}$ $R^{10}$=alkyl, alkenyl, aryl or heteroaryl Y=(for Z=$CH_3$ or $COR^{11}$) free electron pair or (for Z=$CH_3$) O $R^{11}$=alkyl, $CF_3$ or aryl and/or Z=(for Y=O or free electron pair) $CH_3$ or (for Y=free electron pair) $COR^{11}$.

Alkyl may be branched, unbranched or cyclic $C_{1-20}$alkyl, especially $C_{1-7}$alkyl, preferably $C_{1-6}$alkyl and more preferably $C_{1-4}$alkyl, especially methyl, ethyl, propyl, isopropyl, n-butyl, isobutyl, sec-butyl, tert-butyl. Cycloalkyl has preferably from 3 to 8 carbon atoms in the ring.

Alkenyl groups may be branched, unbranched or cyclic $C_{2-20}$alkenyl, especially $C_{2-7}$alkenyl, preferably $C_{2-6}$alkenyl and more preferably $C_{2-4}$alkenyl, especially vinyl, allyl, propen-1-yl, propen-2-yl, but-1-en-1-yl, but-1-en-2-yl, but-1-en-3-yl, but-1-en-4-yl, but-2-en-1-yl, but-2-en-2-yl, 2-methyl-propen-1-yl, 2-methyl-propen-3-yl. Cycloalkenyl has preferably from 3 to 8 carbon atoms in the ring. The number of double bonds in the alkenyl groups may be from 1 to 3.

Aryl may be phenyl, naphthyl and biphenylyl.

Heteroaryl may be furyl, thienyl, imidazolyl, indolyl, pyridinyl, pyrrolyl, thiazolyl, oxazolyl and pyrimidinyl.

Alkyl, alkenyl, aryl and heteroaryl may be unsubstituted or substituted; accordingly they may carry, in any position, from 1 to 3 substituents from the group formed by $C_{1-3}$alkyl, $C_{1-3}$alkoxy, hydroxy, amino ($NH_2$) and nitro ($NO_2$).

A compound according to the invention may accordingly have:

R, $R^1$, $R^4$, $R^5$, $R^8$, $R^9$, $R^{10}$ and/or $R^{11}$=unsubstituted or substituted phenyl, especially $C_{1-4}$alkyl-substituted phenyl $R^5$=$C_{1-4}$alkyl, $C_{2-4}$alkenyl or pyridyl $R^5$ and/or X=$C_{2-4}$alkenyl $R^6$=an alkali metal ion, especially the Na ion, or an alkaline earth metal ion $R^8$ and/or $R^9$=$C_{2-4}$alkenyl and/or $R^{10}$=$C_{2-6}$alkenyl, especially $C_{2-4}$alkenyl, or pyridyl.

A further embodiment of the invention (scheme 1) relates to a process for the preparation of a compound of the general formula I (type 7) wherein R=$OR^1$, $R^1$=H, S=U=H, T=H or OH, V=OR⁷, R⁷=COR⁸, R⁸=alkyl, preferably $C_{1-4}$alkyl, especially methyl, W=H, X=CH₂OR⁹, R⁹=H, Y=free electron pair and Z=CH₃, in which process a compound of the following general formula II (type 1, 2, 3, 4, 5 or 6):

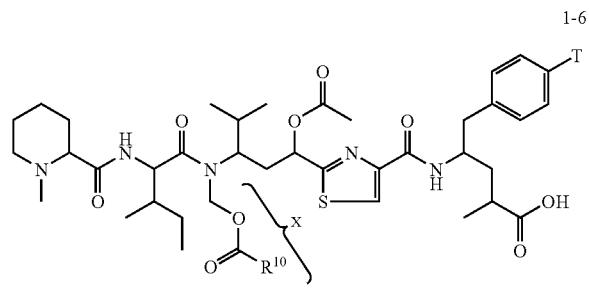

wherein X=CH₂OR⁹, R⁹=COR¹⁰, R¹⁰=alkyl and especially $C_{1-6}$alkyl and which otherwise has the meanings indicated above is subjected to ester cleavage in an acidic medium and the compound of the general formula I having the indicated meanings is obtained.

In the process according to the invention, the ester cleavage can be carried out in an organic solvent, especially dioxane, in the presence of an acid, especially hydrogen chloride, and/or at elevated temperature.

A further embodiment of the invention (scheme 1) relates to a process for the preparation of a compound of the general formula I (type 8) wherein R=OR¹, R¹=H, S=U=H, T=H or OH, V=OR⁷, R⁷=COR⁸, R⁸=alkyl and especially $C_{1-4}$alkyl, especially methyl, W=H, X=H, Y=free electron pair and Z=CH₃, in which process a compound of the general formula II (type 1, 2, 3, 4, 5 or 6) wherein X=CH₂OR⁹, R⁹=COR¹⁰, R¹⁰=alkyl and especially $C_{1-6}$alkyl and which otherwise has the meanings indicated above is subjected to acetal cleavage and the compound of the general formula I having the indicated meanings is obtained.

In the process according to the invention, the acetal cleavage can be carried out in an acidic medium, especially in the presence of hydrochloric acid, and/or at elevated temperature.

A further embodiment of the invention (scheme 1) relates to a process for the preparation of a compound of the general formula I (type 9) wherein R=OR¹, R¹=H, S=U=H, T=H or OH, V=OR⁷, R⁷=H, W=H, X=CH₂OR⁹, R⁹=COR¹⁰, R¹⁰=alkyl and especially $C_{1-6}$alkyl, Y=free electron pair and Z=CH₃, in which process a compound of the general formula II (type 1, 2, 3, 4, 5 or 6) wherein V=OR⁷, R⁷=COR⁸, R⁸=alkyl, preferably $C_{1-4}$alkyl, especially methyl, and which otherwise has the meanings indicated above is subjected to ester cleavage in a weakly alkaline medium and the compound of the general formula I having the indicated meanings is obtained.

In the process according to the invention, the ester cleavage can be carried out in an organic medium, especially a hydrophilic organic solvent, preferably an alcohol, especially methanol, in the presence of a weak base, especially NH₃.

A further embodiment of the invention (scheme 1) relates to a process for the preparation of a compound of the general formula I (type 10) wherein R=OR¹, R¹=H, S=U=H, T=H or OH, V=OR⁷, R⁷=H, W=H, X=H, Y=free electron pair and Z=CH₃, in which process a compound of the general formula II (type 1, 2, 3, 4, 5 or 6) wherein V=OR⁷, R⁷=COR⁸, R⁸=alkyl, preferably $C_{1-4}$alkyl, especially methyl, X=CH₂OR⁹, R⁹=COR¹⁰, R¹⁰=alkyl and especially $C_{1-6}$alkyl and which otherwise has the meanings indicated above is subjected to double ester cleavage in a strongly alkaline medium and the compound of the general formula I having the indicated meanings is obtained.

In the process according to the invention, the double ester cleavage can be carried out in an organic medium, especially in a hydrophilic organic solvent, preferably an alcohol, especially methanol, in the presence of a strong base, especially an alkali metal hydroxide, preferably sodium hydroxide.

A further embodiment of the invention (scheme 1) relates to a process for the preparation of a compound of the following general formula III (type 11):

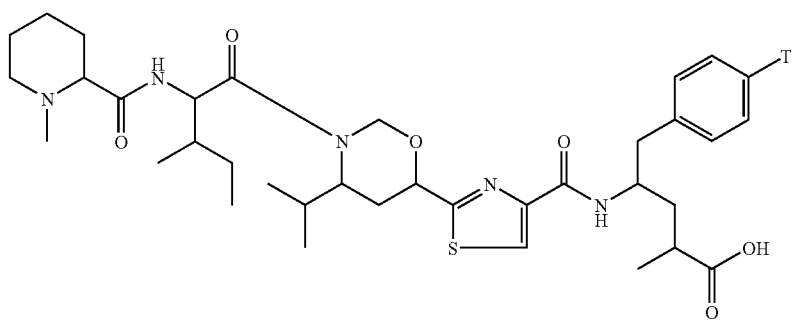

wherein R=OR¹, R¹=H, S=U=H, T=H or OR⁴, R⁴=H, V with X=CH₂O bridge, W=H, Y=free electron pair and Z=CH₃ in the general formula I, in which process a compound of the general formula II (type 1, 2, 3, 4, 5 or 6) wherein X=CH₂OR⁹, R⁹=COR¹⁰, R¹⁰=alkyl and especially $C_{1-6}$alkyl, V=OR⁷, R⁷=COR⁸, R⁸=alkyl, preferably $C_{1-4}$alkyl, especially methyl, and which otherwise has the meanings indicated above is subjected to ring formation with double ester cleavage in an acidic medium and the compound of the general formula above having the indicated meanings is obtained.

In the process according to the invention, the ring formation can be carried out in an aqueous medium, in the presence of an inorganic acid, preferably hydrochloric acid, and with heating.

A further embodiment (scheme 2) relates to a process for the preparation of a compound of the general formula I (type 12) wherein R=OR¹, R¹=H, S=U=H, T=H or OR⁴, R⁴=COR⁵, R⁵=alkyl and especially $C_{1-6}$alkyl, alkenyl and especially $C_{2-6}$alkenyl, aryl or heteroaryl, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=R$^5$, Y=free electron pair and Z=CH$_3$, in which process a compound of the following general formula IV (type 7):

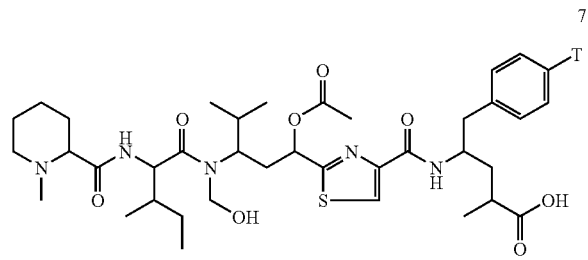

wherein X=CH$_2$OR$^9$, R$^9$=H and which otherwise has the meanings indicated above is subjected to acylation and the compound of the general formula I having the indicated meanings is obtained.

In the process according to the invention, the acylation can be carried out using an acyl halide, especially an acyl chloride, and/or in the presence of a weak base, especially a weak organic base, preferably a tertiary amine, especially triethylamine.

A further embodiment of the invention (scheme 2) relates to a process for the preparation of a compound of the general formula I (type 13) wherein R=OR$^1$, R$^1$=H, S=U=H, T=H or OR$^4$, R$^4$=H, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=alkyl and especially C$_{1-6}$alkyl, alkenyl and especially C$_{2-6}$alkenyl, aryl or heteroaryl, Y=free electron pair and Z=CH$_3$, in which process hydrolysis is carried out in an alkaline medium on a product according to the invention wherein T=OR$^4$, R$^4$=COR$^5$ and R$^5$=alkyl and especially C$_{1-6}$alkyl, alkenyl and especially C$_{2-6}$alkenyl, aryl or heteroaryl and which otherwise has the meanings indicated above, and a compound of the general formula I having the indicated meanings is obtained.

In the process according to the invention, the hydrolysis can be carried out using ammonia.

A further embodiment of the invention (scheme 3) relates to a process for the preparation of a compound of the general formula I (type 14) wherein R=OR$^1$, R$^1$=H, S=U=H, T=H or OH, V=OR$^7$, R$^7$=COR$^8$, R$^8$=alkyl, preferably C$_{1-4}$alkyl, especially methyl, W=H, X=CH$_2$OR$^9$, R$^9$=alkyl and especially C$_{1-4}$alkyl, alkenyl and especially C$_{2-6}$alkenyl or aryl, Y=free electron pair and Z=CH$_3$, in which process a compound of the general formula II (type 1, 2, 3, 4, 5 or 6) is subjected to ester cleavage and is alkylated and a compound of the general formula I having the indicated meanings is obtained.

In the process according to the invention, the reaction can be carried out using an alkylating agent of formula R$^9$OH wherein R$^9$=alkyl and especially C$_{1-4}$alkyl, alkenyl or aryl.

In the process according to the invention, the reaction can be carried out in the presence of p-CH$_3$—C$_6$H$_4$SO$_2$OH in tetrahydrofuran (THF) at elevated temperature.

A further embodiment of the invention (scheme 4) relates to a process for the preparation of a compound of the general formula I (type 15) wherein R=OR$^1$, R$^1$=H, S=U=H, T=H or OR$^4$, R$^4$=H, V=OR$^7$, R$^7$=H or COR$^8$, R$^8$=alkyl, preferably C$_{1-4}$alkyl, especially methyl, W=H, X=CH$_3$, Y=free electron pair and Z=CH$_3$, in which process a compound of the general formula IV (type 7) wherein X=CH$_2$OR$^9$, R$^9$=H and which otherwise has the meanings indicated above is subjected to reduction and the compound of the general formula I having the indicated meanings is obtained.

In the process according to the invention, the reduction can be carried out using NaCNBH$_3$ and trifluoroacetic acid in methanol (MeOH).

A further embodiment of the invention (scheme 4) relates to a process for the preparation of a compound of the general formula I (type 15) wherein R=OR$^1$, R$^1$=H, S=U=H, T=H or OR$^4$, R$^4$=H, V=OR$^7$, R$^7$=H or COR$^8$, R$^8$=alkyl, preferably C$_{1-4}$alkyl, especially methyl, W=H, X=CH$_3$, Y=free electron pair and Z=CH$_3$, in which process a compound of the general formula III (type 11) is subjected to ring opening with reduction or to reduction with ring opening and a compound of the general formula I having the indicated meanings is obtained.

In the process according to the invention, the reaction can be carried out in the presence of NaCNBH$_3$ and Me$_3$SiCl in acetonitrile (CH$_3$CN).

A further embodiment of the invention (scheme 5) relates to a process for the preparation of a compound of the general formula I (type 16) wherein R=OR$^1$, R$^1$=H, S=U=H, T=H or OH, V=OR$^7$, R$^7$=COR$^8$, R$^8$=alkyl and especially C$_{1-4}$alkyl, alkenyl or aryl, W=H, X=CH$_2$OR$^9$, R$^9$=COR$^{10}$, R$^{10}$=alkyl and especially C$_{1-6}$alkyl or alkenyl, Y=free electron pair and Z=CH$_3$, in which process a compound of the general formula I according to the invention (type 9) wherein V=OR$^7$ and R$^7$=H and which otherwise has the meanings indicated above is subjected to acylation and the compound of the general formula I having the indicated meanings is obtained.

In the process according to the invention, the acylation can be carried out using an acyl halide of formula R$^8$COCl wherein R$^8$=alkyl and especially C$_{1-4}$alkyl, alkenyl or aryl, especially an acyl chloride, and/or in the presence of a base, especially an organic base, preferably a trialkylamine, especially triethylamine.

A further embodiment of the invention (scheme 5) relates to a process for the preparation of a compound of the general formula I (type 17) wherein R=OR$^1$, R$^1$=H, S=U=H, T=H or OR$^4$, R$^4$=H, V=H or F, W=H, X=CH$_2$OR$^9$, R$^9$=COR$^{10}$, R$^{10}$=alkyl and especially C$_{1-6}$alkyl or alkenyl, Y=free electron pair and Z=CH$_3$, in which process a compound of the general formula I according to the invention (type 9) wherein V=OR$^7$ and R$^7$=H and which otherwise has the meanings indicated above is subjected to catalytic hydrogenation or fluorination and the compound of the general formula I having the indicated meanings is obtained.

In the process according to the invention, for V=H, the hydrogenation can be carried out using palladium-on-carbon in the presence of acetic acid or, for V=F, the fluorination can be carried out using DAST in tetrahydrofuran.

A further embodiment of the invention (scheme 5) relates to a process for the preparation of a compound of the general formula I (type 18) wherein R=OR$^1$, R$^1$=H, S=U=H, T=H or OR$^4$, R$^4$=H, V with W=O, X=CH$_2$OR$^9$, R$^9$=COR$^{10}$, R$^{10}$=alkyl and especially C$_{1-6}$alkyl or alkenyl, Y=free electron pair and Z=CH$_3$, in which process a compound of the general formula I according to the invention (type 9) wherein V=OR$^7$ and R$^7$=H and which otherwise has the meanings indicated above is subjected to oxidation with formation of a ketone and a compound of the general formula I having the indicated meanings is obtained.

In the process according to the invention, the oxidation can be carried out in the presence of TPAP and NMO in dichloromethane.

A further embodiment of the invention (scheme 5) relates to a process for the preparation of a compound of the general formula I (type 19) wherein R=OR$^1$, R$^1$=H, S=U=H, T=H or OH, V=OR$^7$, R$^7$=H, W=alkyl and especially C$_{1-4}$alkyl, X=CH$_2$OR$^9$, R$^9$=COR$^{10}$, R$^{10}$=alkyl and especially C$_{1-6}$alkyl or alkenyl, Y=free electron pair and Z=CH$_3$, in which process a product of the above process according to the invention (type 18) is reacted with a Grignard compound to form the compound of the general formula I having the indicated meanings.

In the process according to the invention, the reaction can be carried out using an organomagnesium compound of formula WMgHal wherein W=alkyl and especially C$_{1-4}$alkyl.

A further embodiment of the invention (scheme 5) relates to a process for the preparation of a compound of the general formula I (type 19) wherein R=OR$^1$, R$^1$=H, S=U=H, T=H or OH, V=OR$^7$, R$^7$=H, W=alkyl and especially C$_{1-4}$alkyl, X=CH$_2$OR$^9$, R$^9$=COR$^{10}$, R$^{10}$=alkyl and especially C$_{1-6}$alkyl or alkenyl, Y=free electron pair and Z=CH$_3$, in which process (i) in a first step a process according to the invention is carried out and a compound according to the invention (type 18) is obtained and then (ii) in a second step the resulting compound according to the invention (type 18) is reacted in a further process according to the invention to form a compound of the general formula I having the indicated meanings and that compound is obtained.

A further embodiment of the invention (scheme 6) relates to a process for the preparation of a compound of the general formula I (type 20) wherein R=OR$^1$, R$^1$=alkyl and especially C$_{1-4}$alkyl or alkenyl, S=U=H, T=H or OR$^4$, R$^4$=H, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=alkyl and especially C$_{1-6}$alkyl, alkenyl and especially C$_{2-6}$alkenyl, aryl or heteroaryl, Y=free electron pair and Z=CH$_3$, in which process a compound of the general formula II (type 1, 2, 3, 4, 5 or 6) or a product of a process according to the invention (type 13) is subjected to alkylation or alkenylation and a compound of the general formula I having the indicated meanings is obtained.

In the process according to the invention, the alkylation or alkenylation can be carried out in the presence of EDC, R$^1$OH wherein R$^1$=alkyl and especially C$_{1-4}$alkyl or alkenyl, and DMAP in methylene chloride.

A further embodiment of the invention (scheme 6) relates to a process for the preparation of a compound of the general formula I (type 21) wherein R=NHR$^1$, NH—NR$^1$R$^2$, NHOR$^1$ or NH(CH$_2$)$_{2-4}$NR$^1$R$^2$, R$^1$ and R$^2$ each independently of the other=H, alkyl and especially C$_{1-6}$alkyl or aryl, S=U=H, T=H or OR$^4$, R$^4$=H, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=alkyl and especially C$_{1-6}$alkyl, alkenyl and especially C$_{2-6}$alkenyl, aryl or heteroaryl, Y=free electron pair and Z=CH$_3$, in which process a compound of the general formula II (type 1, 2, 3, 4, 5 or 6) or a product of a process according to the invention (type 13) is subjected to amination using a compound of formula RH, R having the indicated meanings, and a compound of the general formula I having the indicated meanings is obtained.

In the process according to the invention, the reaction can be carried out (i) in the presence of EDC in methylene chloride or (ii) in the presence of isobutyl chloroformate and triethylamine in THF.

A further embodiment of the invention (scheme 6) relates to a process for the preparation of a compound of the general formula I (type 22) wherein R=alkyl and especially C$_{1-4}$alkyl or alkenyl, S=U=H, T=H or OR$^4$, R$^4$=H, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=alkyl and especially C$_{1-6}$alkyl, alkenyl and especially C$_{2-6}$alkenyl, aryl or heteroaryl, Y=free electron pair and Z=CH$_3$, in which process a compound of the general formula II (type 1, 2, 3, 4, 5 or 6) or a product of a process according to the invention (type 13) is reacted with an organolithium compound of formula RLi having the indicated meaning for R to form the compound of the general formula I having the indicated meanings.

A further embodiment of the invention (scheme 6) relates to a process for the preparation of a compound of the general formula I (type 23) wherein R=amino radical of 1-(2-amino-C$_{2-4}$alkyl)-pyrrole-2,5-dione, S=U=H, T=H or OR$^4$, R$^4$=H, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=alkyl and especially C$_{1-6}$alkyl, alkenyl and especially C$_{2-6}$alkenyl, aryl or heteroaryl, Y=free electron pair and Z=CH$_3$, in which process a compound of the general formula II (type 1, 2, 3, 4, 5 or 6) or a product of a process according to the invention (type 13) is subjected to amination using 1-(2-amino-C$_{2-4}$ alkyl)-pyrrole-2,5-dione and the compound of the general formula I having the indicated meanings is obtained.

In the process according to the invention, the amination can be carried out in the presence of EDC in methylene chloride.

A further embodiment of the invention (scheme 7) relates to a process for the preparation of a compound of the general formula I (type 24) wherein R=OR$^1$, R$^1$=H, S=U=H, T=OR$^4$, R$^4$=P(O)(OR$^6$)$_2$ wherein R$^6$=H or alkyl, especially C$_{1-4}$alkyl, or R$^4$=SO$_3$R$^6$ wherein R$^6$=H, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=alkyl and especially C$_{1-6}$alkyl, alkenyl, especially C$_{2-6}$alkenyl, aryl or heteroaryl, Y=free electron pair and Z=CH$_3$, in which process (i) a compound of the general formula II (type 1, 2 or 3) or (ii) a product of a process according to the invention (type 13)

is reacted with (a) a compound of formula P(O)(OR$^6$)$_2$OH wherein R$^6$=H or alkyl and especially C$_{1-4}$alkyl or (b) SO$_3$ and the compound of the general formula I having the indicated meanings is obtained.

In the process according to the invention, the variant (a) can be carried out in the presence of I$_2$ and pyridine in methylene chloride.

In the process according to the invention, the variant (b) can be carried out using pyridine-SO$_3$.

A further embodiment of the invention (scheme 7) relates to a process for the preparation of a compound of the general formula I (type 25) wherein R=OR$^1$, R$^1$=H, S=U=H, T=OR$^4$, R$^4$=COR$^5$, R$^5$=alkyl and especially C$_{1-4}$alkyl, alkenyl or N(R$^{12}$)$_2$, R$^{12}$=alkyl, V=OR$^7$, R$^7$=COR$^8$, R$^8$=alkyl, preferably C$_{1-4}$alkyl, especially methyl, W=H, X=CH$_2$OR$^9$, R$^9$=COR$^{10}$, R$^{10}$=alkyl, especially C$_{1-6}$alkyl, alkenyl, especially C$_{2-6}$alkenyl, aryl or heteroaryl, in which process (i) a compound of the general formula II (type 1, 2 or 3) or (ii) a product of a process according to the invention (type 13)

is subjected to acylation and the compound of the general formula I having the indicated meanings is obtained.

In the process according to the invention, the acylation can be carried out using an acyl halide of formula R$^5$COCl wherein R$^5$=alkyl and especially C$_{1-4}$alkyl, alkenyl or N(R$^{12}$)$_2$ and R$^{12}$=alkyl, especially using an acyl chloride, in the presence of an organic base, especially a trialkylamine, preferably triethylamine, in an organic solvent, especially THF.

A further embodiment of the invention (scheme 7) relates to a process for the preparation of a compound of the general formula I (type 26) wherein R=$OR^1$, $R^1$=alkyl and especially $C_{1-4}$alkyl or alkenyl, S=U=H, T=$OR^4$, $R^4$=alkyl and especially $C_{1-4}$alkyl or alkenyl, V=$OR^7$, $R^7$=$COR^8$, $R^8$=alkyl and especially $C_{1-4}$alkyl, especially methyl, W=H, X=$CH_2OR^9$, $R^9$=$COR^{10}$, $R^{10}$=alkyl, especially $C_{1-6}$alkyl, alkenyl, especially $C_{2-6}$alkenyl, aryl or heteroaryl, Y=free electron pair and Z=$CH_3$, in which process (i) a compound of the general formula II (type 1, 2 or 3) or (ii) a product of a process according to the invention (type 13)

is subjected to alkylation and the compound of the general formula according to claim 1 having the indicated meanings is obtained.

In the process according to the invention, the alkylation can be carried out using an alkyl iodide of formula $R^4I$ wherein $R^4$=alkyl and especially $C_{1-4}$alkyl or alkenyl in the presence of a weak base, especially $Ag_2O$, in an organic solvent, especially methylene chloride.

In the process according to the invention, methylation can be carried out using diazomethane in an organic solvent, especially methanol.

A further embodiment of the invention (scheme 7) relates to a process for the preparation of a compound of the general formula I (type 27) wherein R=$OR^1$, $R^1$=H, S=U=H, T=$OR^4$, $R^4$=alkyl and especially $C_{1-4}$alkyl or alkenyl, V=$OR^7$, $R^7$=$COR^8$, $R^8$=alkyl, preferably $C_{1-4}$alkyl, especially methyl, W=H, X=$CH_2OR^9$, $R^9$=$COR^{10}$, $R^{10}$=alkyl, especially $C_{1-6}$alkyl, alkenyl, especially $C_{2-6}$alkenyl, aryl or heteroaryl, Y=free electron pair and Z=$CH_3$, in which process a product of a process according to the invention (type 26) is subjected to partial dealkylation or dealkenylation enzymatically and the compound of the general formula I having the indicated meanings is obtained.

In the process according to the invention, an esterase, especially pig liver esterase, can be used as the enzyme.

A further embodiment of the invention (scheme 7) relates to a process for the preparation of a compound of the general formula I (type 27) R=$OR^1$, $R^1$=H, S=U=H, T=$OR^4$, $R^4$=alkyl and especially $C_{1-4}$alkyl or alkenyl, V=$OR^7$, $R^7$=$COR^8$, $R^8$=alkyl, preferably $C_{1-4}$alkyl, especially methyl, W=H, X=$CH_2OR^9$, $R^9$=$COR^{10}$, $R^{10}$=$C_{1-6}$alkyl, alkenyl, especially $C_{2-6}$alkenyl, aryl or heteroaryl, in which process (a) in a first step (i) a compound of the general formula II (type 1, 2 or 3) or (ii) a product of a process according to the invention (type 13)

is subjected to a process according to the invention and a compound according to the invention (type 26) is obtained and (b) in a second step the resulting compound according to the invention (type 26) is reacted in a further process according to the invention to form a compound of the general formula I having the indicated meanings and that compound is obtained.

A further embodiment of the invention (scheme 8) relates to a process for the preparation of a compound of the general formula I (type 28 and, as the case may be, 29) wherein R=$OR^1$, $R^1$=H, S=H or Hal, T=$OR^4$, $R^4$=H, U=Hal, V=$OR^7$, $R^7$=$COR^8$, $R^8$=alkyl and especially $C_{1-4}$alkyl, especially methyl, W=H, X=$CH_2OR^9$, $R^9$=$COR^{10}$, $R^{10}$=alkyl and especially $C_{1-6}$alkyl, alkenyl, especially $C_{2-6}$alkenyl, aryl or heteroaryl, in which process (i) a compound of the general formula II (type 1, 2, 3, 4, 5 or 6) or (ii) a product of a process according to the invention (type 13)

is subjected to halogenation or dihalogenation in the position ortho to the T substituent and the compound of the general formula I having the indicated meanings is obtained.

In the process according to the invention, the halogenation can be carried out in the presence of $C_5Cl_5NF$-triflate, $SO_2Cl_2$, NBS and ICl.

A further embodiment of the invention (scheme 8) relates to a process for the preparation of a compound of the general formula I (type 30) wherein R=$OR^1$, $R^1$=H, S=H, T=$OR^4$, $R^4$=H, U=$NO_2$, V=$OR^7$, $R^7$=$COR^8$, $R^8$=alkyl, preferably $C_{1-4}$alkyl, especially methyl, W=H, X=$CH_2OR^9$, $R^9$=$COR^{10}$, $R^{10}$=alkyl, especially $C_{1-6}$alkyl, alkenyl, especially $C_{2-6}$alkenyl, aryl or heteroaryl, Y=free electron pair and Z=$CH_3$, in which process (i) a compound of the general formula II (type 1, 2, 3, 4, 5 or 6) or (ii) a product of a process according to the invention (type 13)

is subjected to nitration in the position ortho to the T substituent and the compound of the general formula I having the indicated meanings is obtained.

In the process according to the invention, the nitration can be carried out using an alkali metal nitrite, especially sodium nitrite, and acetic acid in the presence of an organic solvent, especially ethanol.

A further embodiment of the invention (scheme 8) relates to a process for the preparation of a compound of the general formula I (type 31) wherein R=$OR^1$, $R^1$=H, S=H, T=$OR^4$, $R^4$=H, U=$NH_2$, V=$OR^7$, $R^7$=$COR^8$, $R^8$=alkyl, preferably $C_{1-4}$alkyl, especially methyl, W=H, X=$CH_2OR^9$, $R^9$=$COR^{10}$, $R^{10}$=alkyl and especially $C_{1-6}$alkyl, alkenyl, especially $C_{2-6}$alkenyl, aryl or heteroaryl, Y=free electron pair and Z=$CH_3$, in which process a product of a process according to the invention (type 30) is subjected to catalytic reduction and the compound of the general formula I having the indicated meanings is obtained. In the process according to the invention, the reduction can be carried out using elemental hydrogen in the presence of palladium on activated carbon, especially in an organic solvent, preferably ethanol.

A further embodiment of the invention (scheme 8) relates to a process for the preparation of a compound of the general formula I (type 31) wherein R=$OR^1$, $R^1$=H, S=H, T=$OR^4$, $R^4$=H, U=$NH_2$, V=$OR^7$, $R^7$=$COR^8$, $R^8$=alkyl, preferably $C_{1-4}$alkyl, especially methyl, W=H, X=$CH_2OR^9$, $R^9$=$COR^{10}$, $R^{10}$=alkyl and especially $C_{1-6}$alkyl, alkenyl, especially $C_{2-6}$alkenyl, aryl or heteroaryl, Y=free electron pair and Z=$CH_3$, in which process (a) in a first step (i) a compound of the general formula II (type 1, 2, 3, 4, 5 or 6) or (ii) a product of a process according to the invention (type 13)

is subjected to a further process according to the invention and a compound according to the invention (type 30) is obtained and (b) in a second step the resulting product (type 30) is subjected to a further process according to the invention and the compound of the general formula I having the indicated meanings is obtained.

A further embodiment of the invention (scheme 8) relates to a process for the preparation of a compound of the general formula I (type 32) wherein $R=OR^1$, $R^1=H$, $S=H$, $T=OR^4$, $R^4=H$, $U=NHR^3$, $R^3$=alkyl-CO and especially $C_{1-4}$alkyl-CO, $V=OR^7$, $R^7=COR^8$, $R^8$=alkyl, preferably $C_{1-4}$alkyl, especially methyl, $W=H$, $X=CH_2OR^9$, $R^9=COR^{10}$, $R^{10}$=alkyl and especially $C_{1-6}$alkyl, alkenyl, especially $C_{2-6}$alkenyl, aryl or heteroaryl, $Y$=free electron pair and $Z=CH_3$, in which process a product of a process according to the invention (type 31) is subjected to alkylation and the compound of the general formula I having the indicated meanings is obtained.

In the process according to the invention, the alkylation can be carried out using an acid anhydride of formula $(R^3)_2O$ wherein $R^3=CO—C_{1-4}$alkyl.

A further embodiment of the invention (scheme 8) relates to a process for the preparation of a compound of the general formula I (type 32) wherein $R=OR^1$, $R^1=H$, $S=H$, $T=OR^4$, $R^4=H$, $U=NHR^3$, $R^3$=alkyl-CO and especially $C_{1-4}$alkyl-CO, $V=OR^7$, $R^7=COR^8$, $R^8$=alkyl, preferably $C_{1-4}$alkyl, especially methyl, $W=H$, $X=CH_2OR^9$, $R^9=COR^{10}$, $R^{10}$=alkyl, preferably $C_{1-6}$alkyl, alkenyl, especially $C_{2-6}$alkenyl, aryl or heteroaryl, in which process (a) in an optional first step (i) a compound of the general formula II (type 1, 2, 3, 4, 5 or 6) or (ii) a product of a process according to the invention (type 13)

is subjected to a further process according to the invention, (b) in a second step the resulting product (type 30) is subjected to a further process according to the invention and (c) in a third step the resulting compound according to the invention (type 31) is subjected to a further process according to the invention and the compound of the general formula I having the indicated meanings is obtained.

A further embodiment of the invention (scheme 9) relates to a process for the preparation of a compound of the general formula I (type 33) wherein $R=OR^1$, $R^1=H$, $S=U=H$, $T=OR^4$, $R^4=H$, $V=OR^7$, $R^7=COR^8$, $R^8$=alkyl, preferably $C_{1-4}$alkyl, especially methyl, $W=H$, $X=CH_2OR^9$, $R^9=COR^{10}$, $R^{10}$=alkyl and especially $C_{1-6}$alkyl, alkenyl, especially $C_{2-6}$alkenyl, aryl or heteroaryl, $Y=O$ and $Z=CH_3$, in which process (i) a compound of the general formula II (type 1, 2, 3, 4, 5 or 6) or (ii) a product of a process according to the invention (type 13)

is subjected to a reaction for formation of an N-oxide and the compound of the general formula I having the indicated meanings is obtained.

In the process according to the invention, the N-oxide formation can be carried out using m-CPBA in an organic solvent, especially methylene chloride.

A further embodiment of the invention (scheme 9) relates to a process for the preparation of a compound of the general formula I (type 34) wherein $R=OR^1$, $R^1=H$, $S=U=H$, $T=OR^4$, $R^4=H$, $V=OR^7$, $R^7=COR^8$, $R^8$=alkyl, preferably $C_{1-4}$alkyl, especially methyl, $W=H$, $X=CH_2OR^9$, $R^9=COR^{10}$, $R^{10}$=alkyl and especially $C_{1-6}$alkyl, alkenyl, especially $C_{2-6}$alkenyl, aryl or heteroaryl, $Y$=free electron pair, $Z=COR^{11}$ and $R^{11}$=alkyl, preferably $C_{1-4}$alkyl, especially methyl, in which process the product of a process according to the invention (type 33) is reacted with an acylating agent and the compound of the general formula I having the indicated meanings is obtained.

In the process according to the invention, the acylation can be carried out using an acid anhydride, especially acetic anhydride, preferably at elevated temperature.

A further embodiment of the invention (scheme 9) relates to a process for the preparation of a compound of the general formula I (type 34) wherein $R=OR^1$, $R^1=H$, $S=U=H$, $T=OR^4$, $R^4=H$, $V=OR^7$, $R^7=COR^8$, $R^8$=alkyl, preferably $C_{1-4}$alkyl, especially methyl, $W=H$, $X=CH_2OR^9$, $R^9=COR^{10}$, $R^{10}$=alkyl and especially $C_{1-6}$alkyl, alkenyl, especially $C_{2-6}$alkenyl, aryl or heteroaryl, $Y$=free electron pair, $Z=COR^{11}$ and $R^{11}$=alkyl, preferably $C_{1-4}$alkyl, especially methyl, in which process (a) in a first step (i) a compound of the general formula II (type 1, 2, 3, 4, 5, or 6) or (ii) a product of a process according to the invention (type 13) is subjected to a process according to the invention and (b) in a second step the resulting product (type 33) is subjected to a further process according to the invention and the compound of the general formula according to claim 1 having the indicated meanings is obtained.

A further embodiment of the invention relates to a therapeutic preparation, especially a cytostatic agent, comprising one or more compounds according to the invention as active ingredient in addition to one or more optional customary carriers and/or one or more optional customary diluents.

Finally, an embodiment of the invention relates to a therapeutic preparation, especially a cytostatic agent, comprising one or more products of a process according to the invention as active ingredient in addition to one or more optional customary carriers and/or one or more optional customary diluents.

Figure 1:
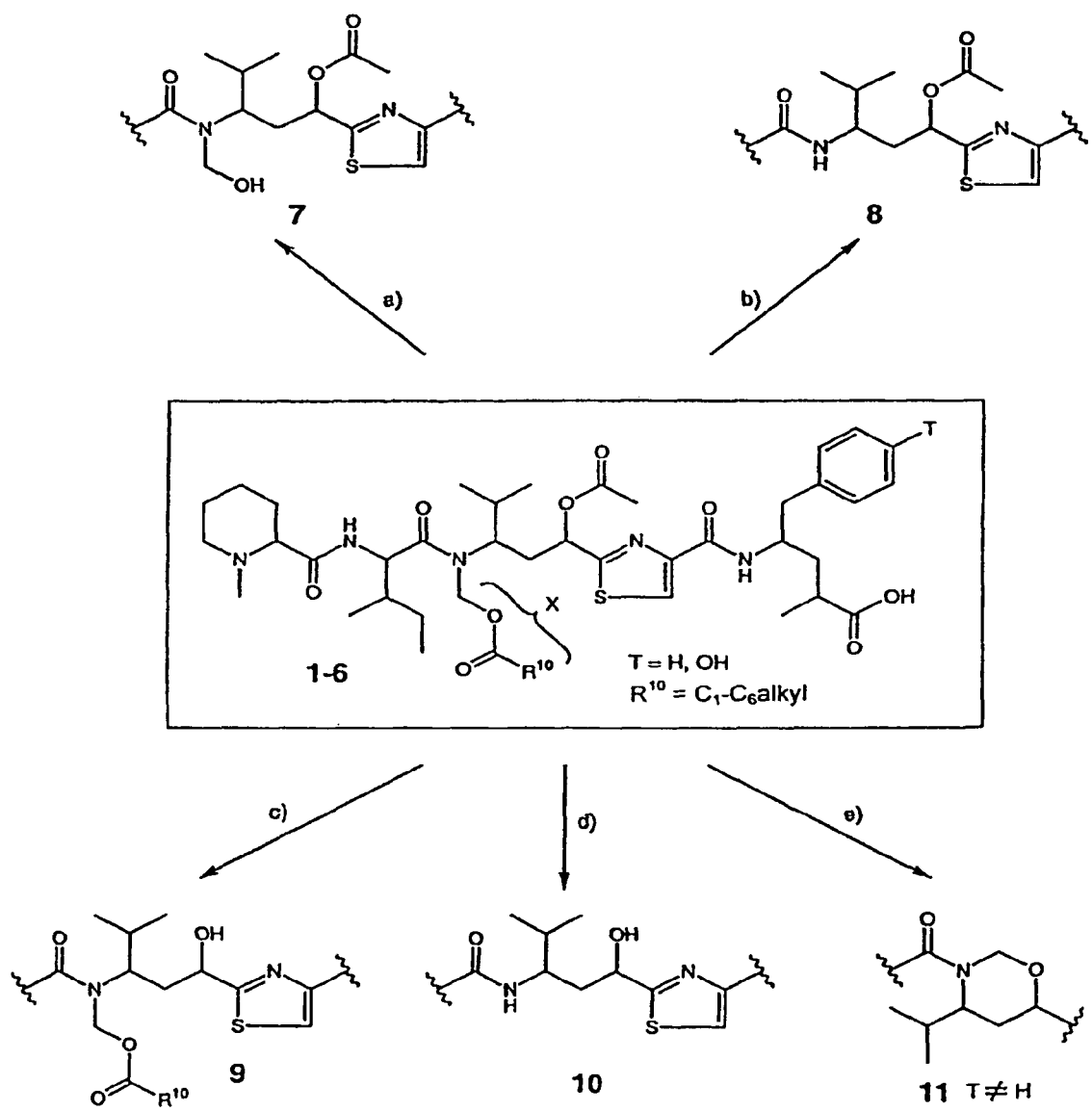
FIG. 1 depicts the generic procedures for making tubulysin derivative compounds which encompass the compounds associated with scheme 1.
Figure 2:
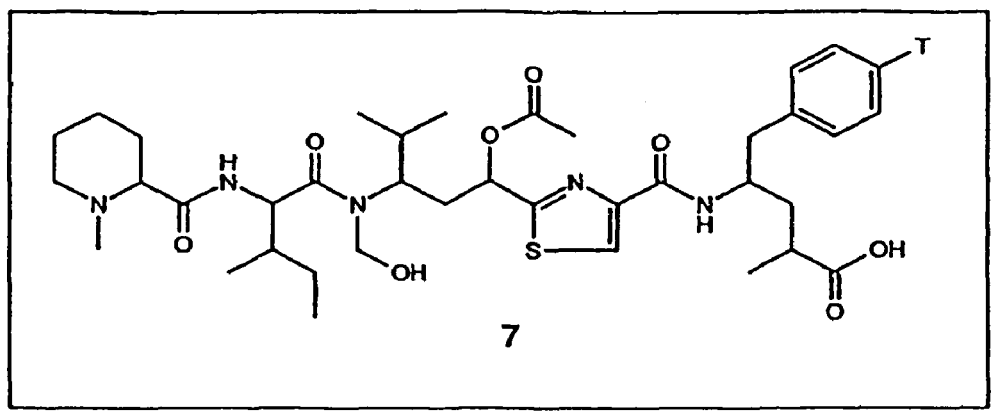
FIG. 2 depicts the generic procedures for making tubulysin derivative compounds which encompass tubulysin derivatives 12 and 13.
Figure 2:
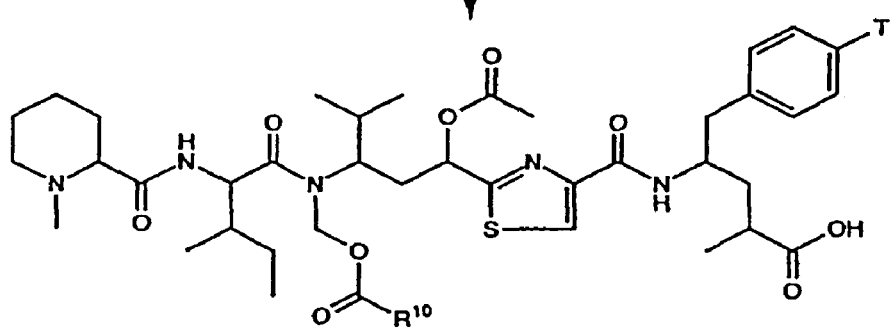
Figure 2:
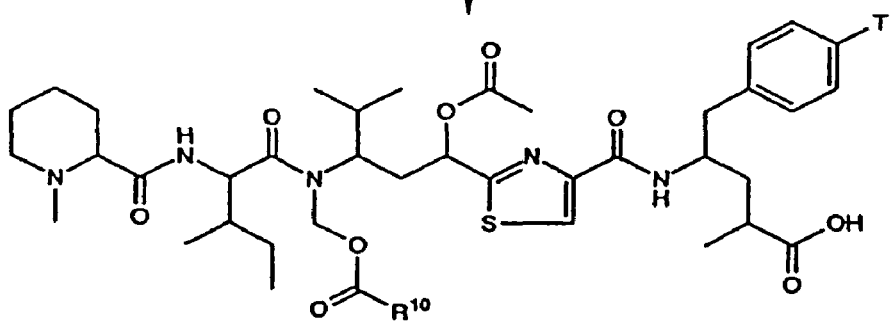
Figure 3:
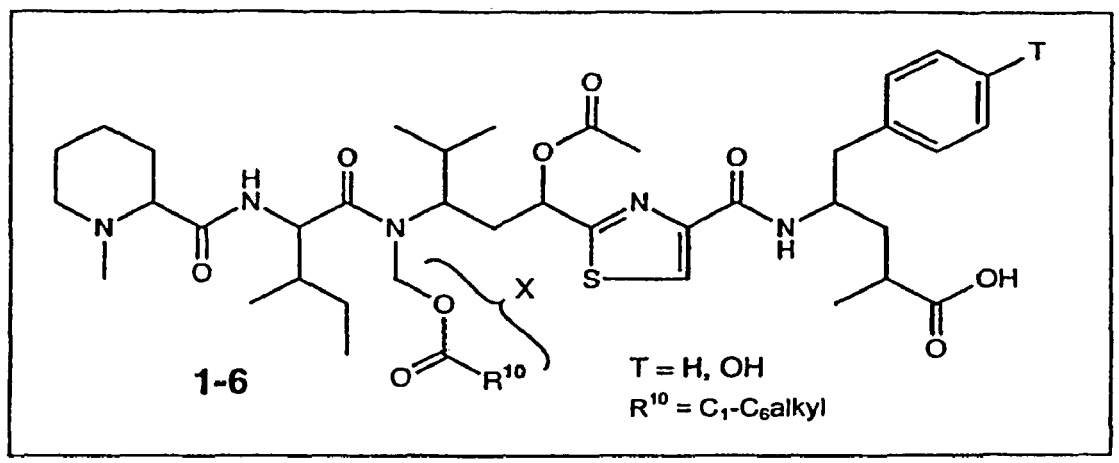
FIG. 3 depicts the generic procedures for making tubulysin derivative compounds which encompass the compounds associated with scheme 3.
Figure 3:
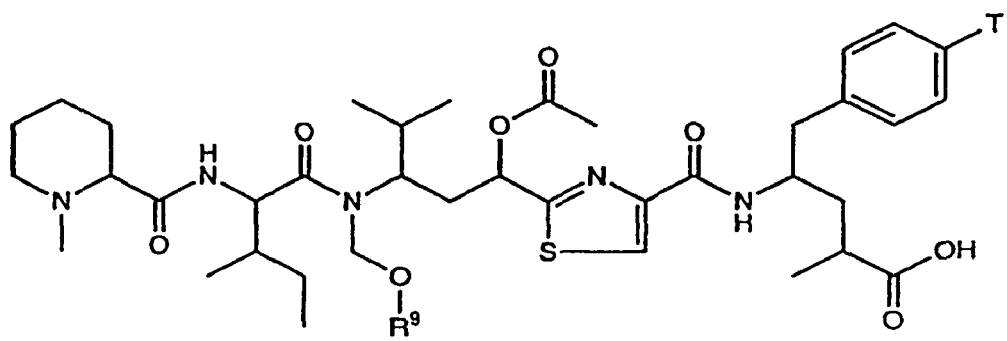
Figure 4:
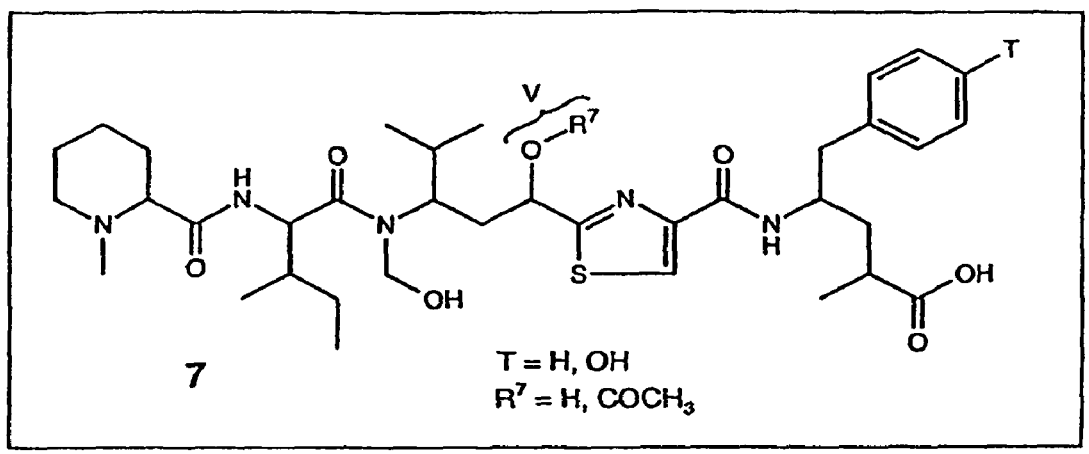
FIG. 4 depicts the generic procedures for making tubulysin derivative compounds which encompass the tubulysin derivative 15.
Figure 4:
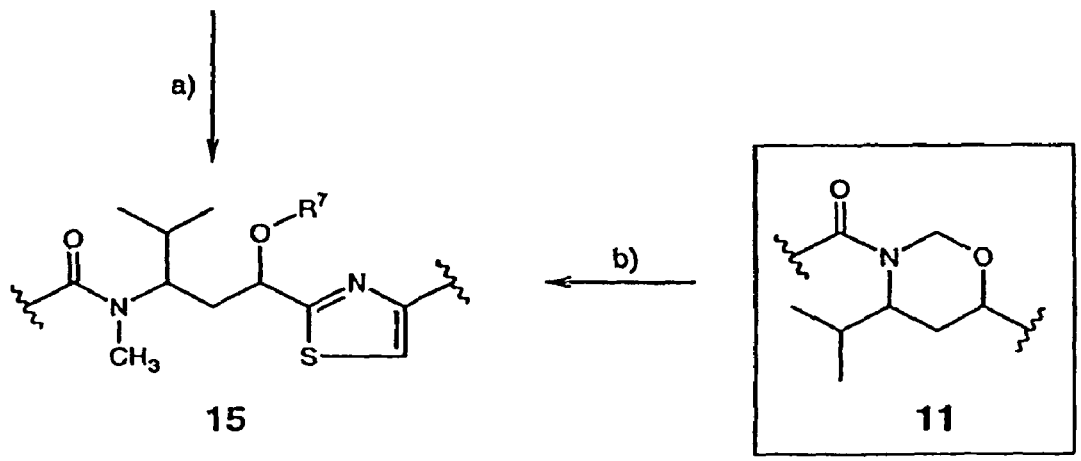
Figure 5:
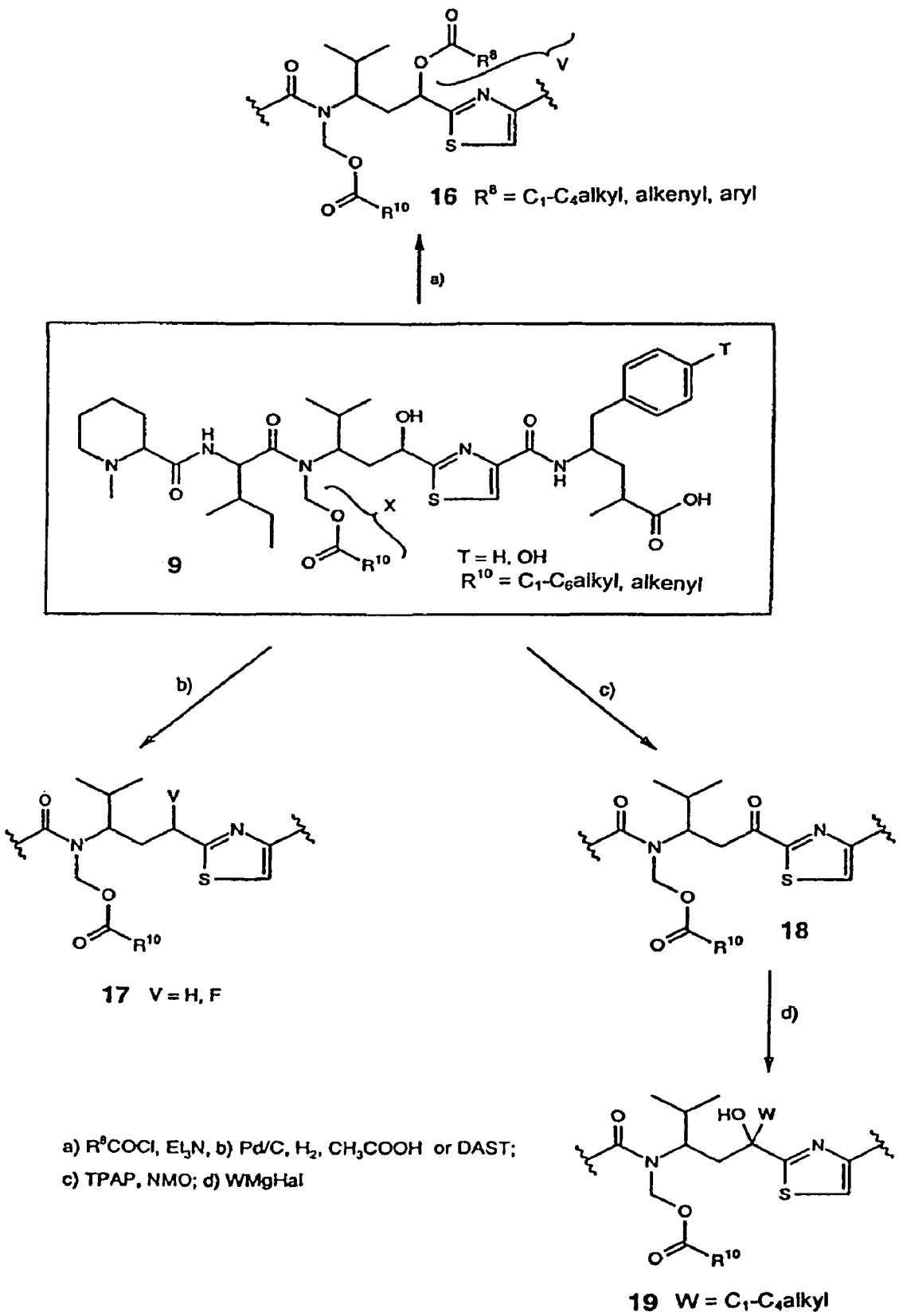
FIG. 5 depicts the generic procedures for making tubulysin derivative compounds which encompass the tubulysin derivatives 16-19.
Figure 6:
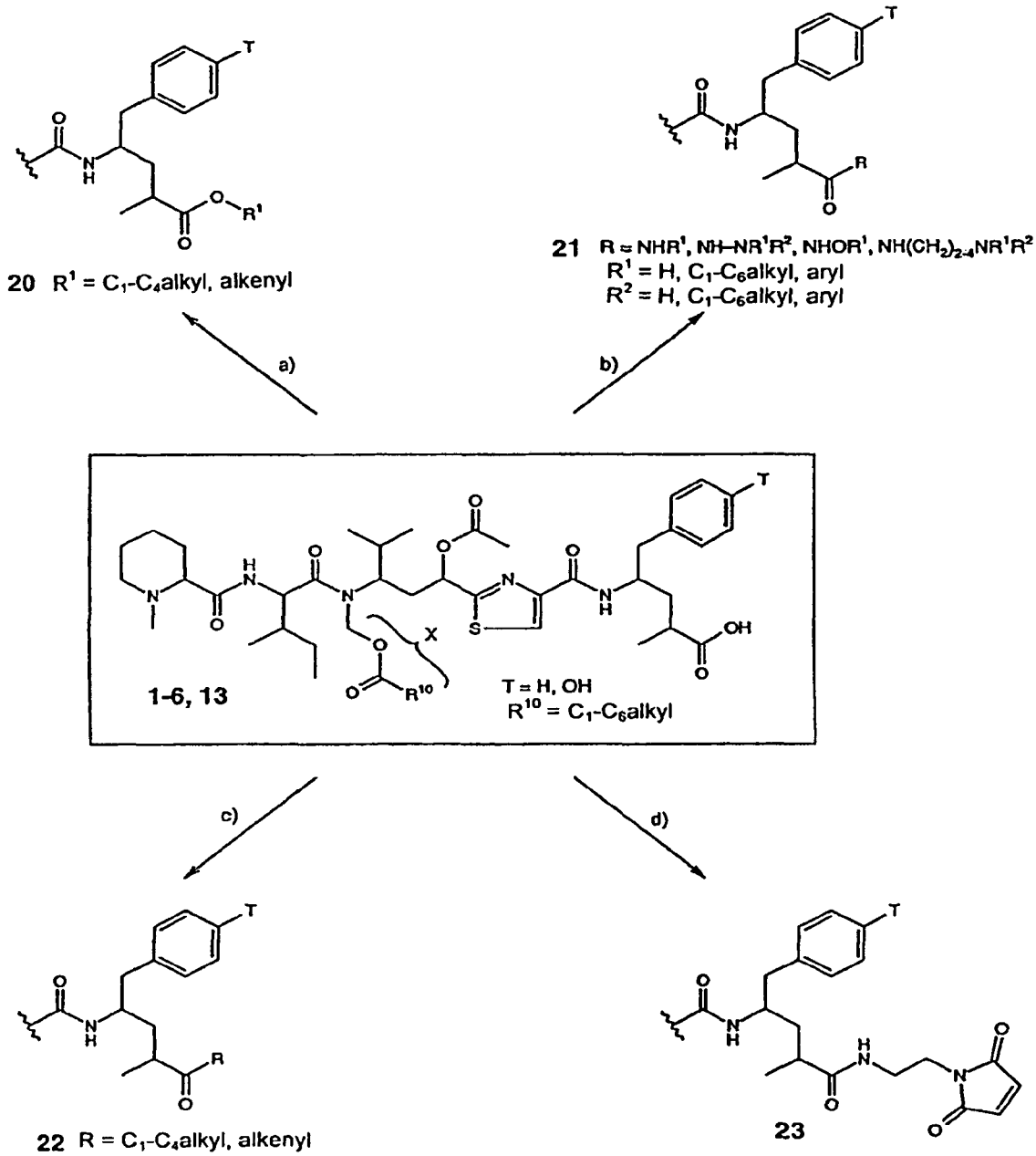
FIG. 6 depicts the generic procedures for making tubulysin derivative compounds which encompass the compounds associated with scheme 6.
Figure 7:
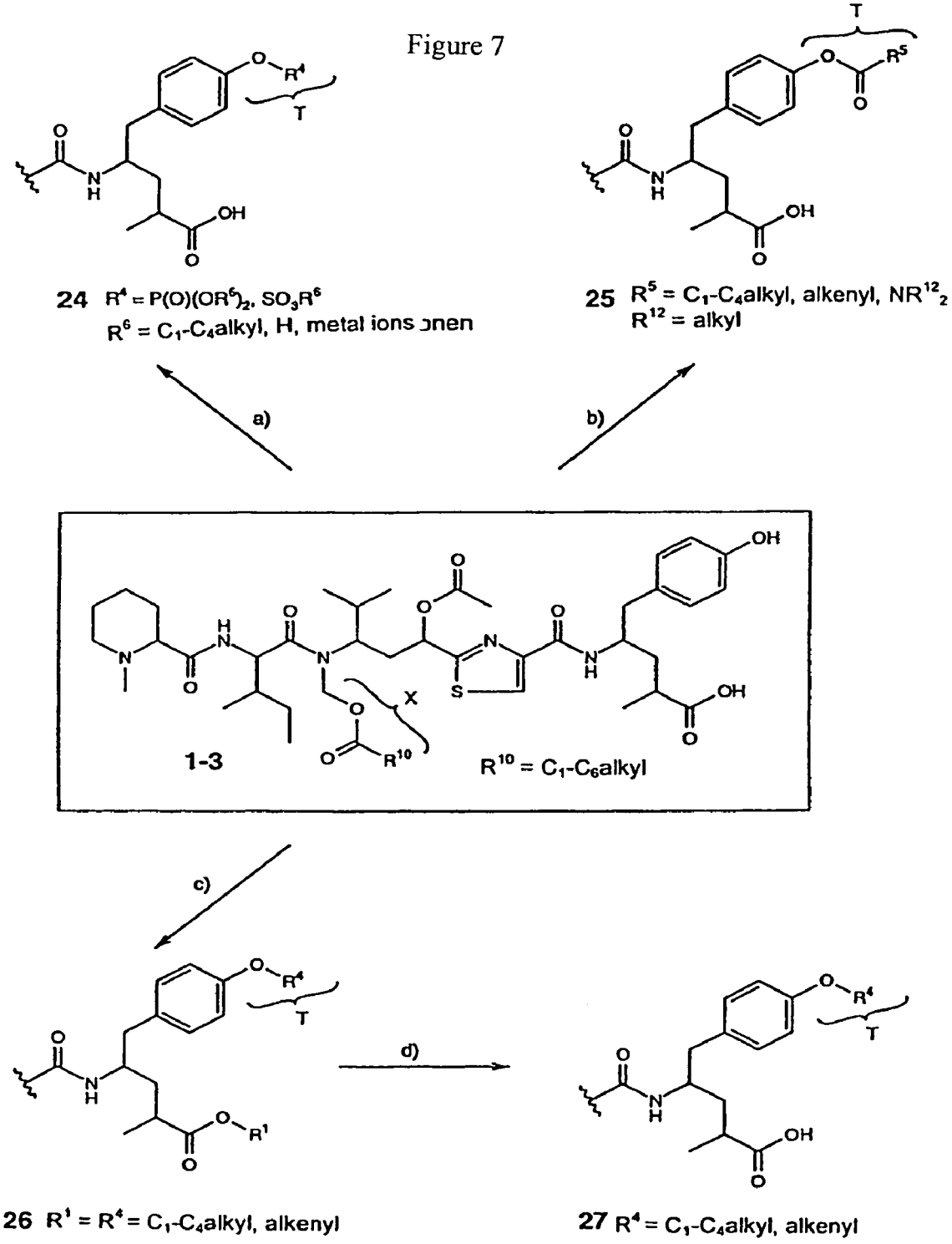
FIG. 7 depicts the generic procedures for making tubulysin derivative compounds which encompass the compounds associated with scheme 7.
Figure 8:
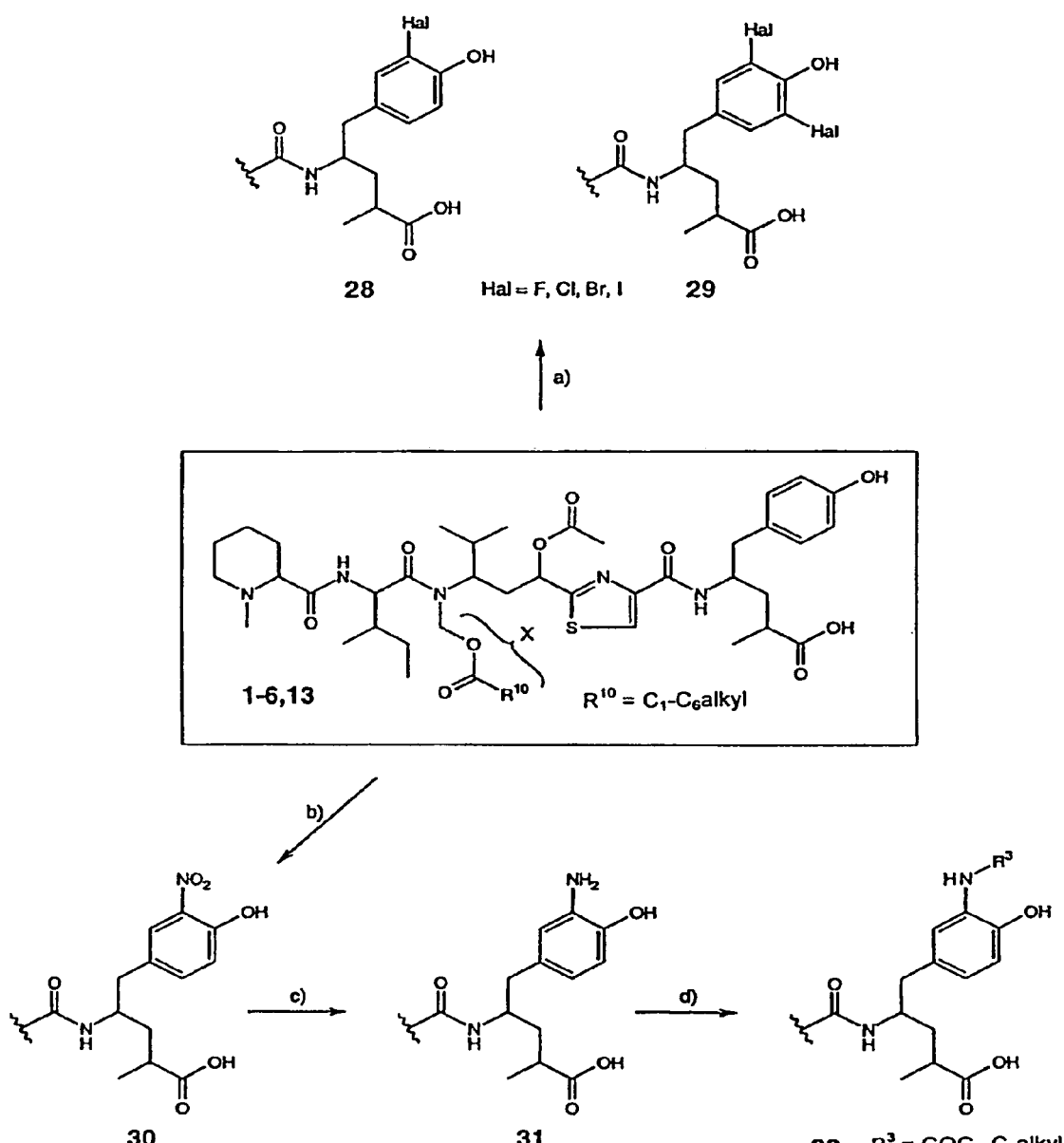
FIG. 8 depicts the generic procedures for making tubulysin derivative compounds which encompass the compounds associated with scheme 8.
Figure 9:
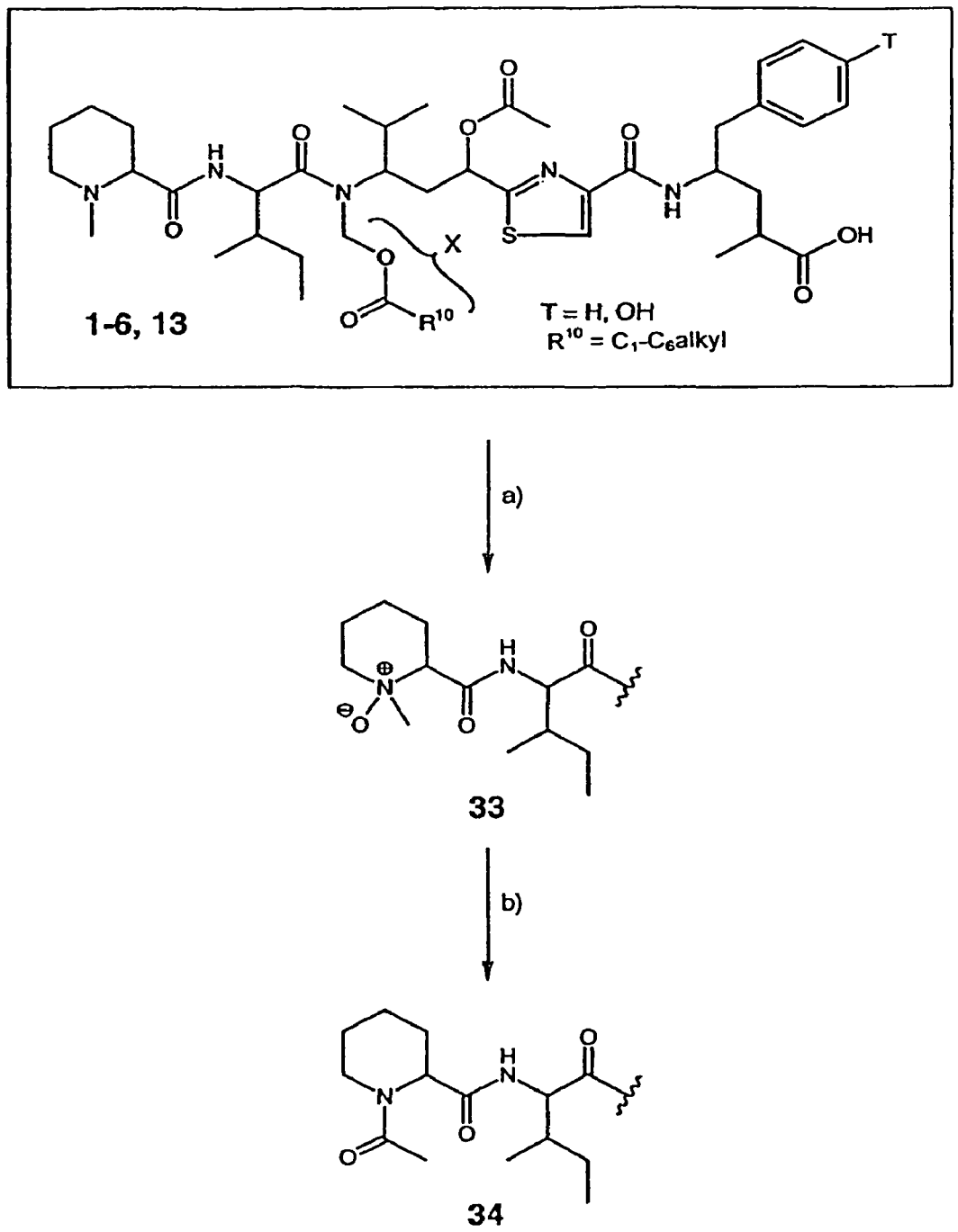
FIG. 9 depicts the generic procedures for making tubulysin derivative compounds which encompass the compounds associated with scheme 9.

The invention is described hereinbelow in greater detail by means of Examples.

Tubulysin Derivative 7a: $R^1$=OH (Scheme 1)

9.9 mg (11.7 µmol) of tubulysin A (1) were dissolved in 200 µl of dioxane and 1 ml of 0.1M hydrochloric acid solution was added. The reaction mixture was stirred at 50° C. for 8 hours. The mixture was then lyophilised and the residue subjected to preparative HPLC (CH$_3$CN/H$_2$O 35/65 with 50 mM NH$_4$Ac, pH=6.5), whereupon 5.3 mg (59%) of 7a were obtained.

$R_f$ 0.55; $[\alpha]^{22}_D$ –7.0 (c 0.89 MeOH); UV (MeOH): $\lambda_{max}$ nm (lg ε) 226 (4.13), 250 (3.91); IR (KBr): $\nu_{max}$ 3386, 2963, 2934, 1655, 1546, 1232 cm$^{-1}$; $^1$H NMR (DMSO-d$_6$ 600 MHz): as tubulysin A (1) except Tuv δ 8.06 (1H, s, H-3), 6.18 (1H, d, J=11.9 Hz, H-11b), 5.37 (1H, d, J=11.8 Hz, H-11a), 4.63 (1H, br, H-5), 4.10 (1H, br, H-7), 2.20 (1H, m, H-6b), 1.99 (1H, m, H-8), 1.98 (1H, m, H-6a), 1.91 (1H, m, H-2'b), 1.48 (1H, m, H-3'b), 1.44 (1H, m, H-3'a), 1.42 (1H, m, H-2'a), 0.92 (3H, d, J=6.4 Hz, H-9), 0.80 (3H, t, J=7.3 Hz, H4'), 0.73 (3H, d, J=6.2 Hz, H-10); $^{13}$C NMR (DMSO-d$_6$ 150 MHz): as tubulysin A (1) except Tuv δ 178.0 (s, C-4), 174.4 (s, C-1'), 160.0 (s, C-1), 149.6 (s, C-2), 123.0 (d, C-3), 68.0 (t, C-11), 67.5 (d, C-5), 55.0 (d, C-7), 37.4 (t, C-2'), 35.7 (t, C-6), 30.6 (d, C-8), 20.1 (q, C-9), 19.5 (q, C-10), 17.7 (t, C-3'), 13.3 (q, C-4'); DCI MS: m/z [M+H]$^+$ 760 (4); HRMS (DCI): C$_{38}$H$_{58}$N$_5$O$_9$S: 760.3917 [M+H$^+$](calc.: 760.3955).

Tubulysin Derivative 8a: $R^1$=OH (Scheme 1)

500 µl of 0.1M hydrochloric acid were added to 20.0 mg (23.7 µmol) of tubulysin A (1). The reaction mixture was stirred for 5 minutes at 100° C., was then cooled and was neutralised (pH=7) using saturated NaHCO$_3$ solution. Extraction was then carried out three times using ethyl acetate, and the combined organic phases were concentrated. The crude product was purified by means of preparative HPLC (CH$_3$CN/H$_2$O 35/65 with 50 mM NH$_4$Ac, pH=6.5), whereupon 6.4 mg (37%) of 8a, 2.7 mg (15%) of 7a and 5.1 mg (31%) of 10a were obtained.

8a:

$R_f$ 0.55; $[\beta]^{22}_D$ –10.2 (c 1.0 MeOH); UV (MeOH): $\lambda_{max}$ nm (lg ε) 225 (4.10), 250 (3.94); IR (KBr): $\nu_{max}$ 3389, 3251, 2962, 2934, 1658, 1547, 1228 cm$^{-1}$; $^1$H NMR (DMSO-d$_6$ 600 MHz): as tubulysin A (1) except Tuv δ 8.17 (1H, s, H-3), 7.92 (1H, br, NH-7), 5.76 (1H, dd, J=10.5, 3.0 Hz, H-5), 3.86 (1H, m, H-7), 2.13 (1H, m, H-6b), 2.09 (3H, s, H-5OAc), 1.95 (1H, m, H-6a), 1.73 (1H, m, H-8), 0.84 (3H, d, J=6.4 Hz, H-10), 0.83 (3H, d, J=6.0 Hz, H-9), Ile δ 7.54 (1H, d, J=9.3 Hz, NH-2), 4.18 (1H, dd, J=9.1 Hz, H-2), 1.75 (1H, m, H-3), 1.48 (1H, m, H-4b), 1.07 (1H, m, H-4a), 0.85 (3H, m, H-6), 0.81 (3H, m, H-5); $^{13}$C NMR (DMSO-d$_6$ 150 MHz): as tubulysin A (1) except Tuv δ 169.6 (s, C-5OAc), 169.6 (s, C-4), 159.8 (s, C-1), 149.8 (s, C-2), 124.0 (d, C-3), 69.5 (d, C-5), 49.5 (d, C-7), 36.4 (t, C-6), 31.7 (d, C-8), 20.6 (q, C-5OAc), 18.9 (q, C-9), 18.0 (q, C-10), Ile δ 171.1 (s, C-1), 56.7 (d, C-2), 36.2 (d, C-3), 24.3 (t, C-4), 15.6 (q, C-6), 10.6 (q, C-5); DCI MS: m/z [M+H]$^+$ 730 (100), 672 (15); HRMS (DCI): C$_{37}$H$_{56}$N$_5$O$_8$S: 730.3839 [M+H]$^+$ (calc.: 730.3850).

Tubulysin Derivative 9a: R=iso-C$_4$H$_9$, $R^1$=OH (Scheme 1)

9.6 mg (11.4 µmol) of tubulysin A (1) were dissolved in 1 ml of methanol and, at intervals of three hours, 10 µl (133.6 µmol) of 25% ammonia were added on each occasion and stirring was carried out at room temperature. The reaction mixture was then adjusted to pH 5 using 18% hydrochloric acid and extracted three times with ethyl acetate. The combined organic phases were concentrated and purified by means of PLC (CH$_2$Cl$_2$/MeOH 85/15). 2.5 mg (27%) of 9a, 2.3 mg (29%) of 10a and 1.7 mg (18%) of 1 were isolated.

9a:

ESI MS (1 eV): 802 [M+H]$^+$; $^1$H NMR (DMSO-d$_6$, 600 MHz): δ=4.63 (br, 1H, H-5), 4.10 (br, 1H, H-7), 2.20 (m, 1H, H-6b), 1.99 (m, 1H, H-8), 1.98 (m, 1H, H-6a).

Tubulysin Derivative 10a: $R^1$=OH (Scheme 1)

5.4 mg (6.8 µmol) of tubulysin A (1) were dissolved in 300 µl of methanol, 67.0 µl of 1M sodium hydroxide solution (67.6 µmol) were added and stirring was carried out for 15 minutes at room temperature. The reaction mixture was then diluted with water and adjusted to pH 7 using 1M hydrochloric acid solution. After extracting three times with ethyl acetate, the combined organic phases were concentrated. The residue was purified by means of preparative HPLC (CH$_3$CN/H$_2$O 35/65 with 50 mM NH$_4$Ac, pH=6.5), whereupon 2.5 mg (57%) of 10a were obtained.

$R_f$ 0.40; $[\alpha]^{22}_D$ –3.0 (c 0.66 MeOH); UV (MeOH): $\lambda_{max}$ nm (lg ε) 225, (4.12), 250 (3.92); IR (KBr): $\nu_{max}$ 3376 cm$^{-1}$, 3285, 2960, 2929, 1656, 1547; $^1$H NMR (DMSO-d$_6$ 600 MHz): as tubulysin A (1) except Tuv δ 8.06 (1H, s, H-3), 7.67 (1H, br, NH-7), 4.65 (1H, ddbr, J=8.7 Hz, H-5), 3.97 (1H, m, H-7), 1.98 (1H, m, H-6b), 1.79 (1H, m, H-6a), 1.74 (1H, m, H-8), 0.85 (3H, d, J=6.7 Hz, H-9), 0.84 (3H, d, J=6.2 Hz, H-10), Ile δ 7.75 (1H, br, NH-2), 4.15 (1H, dd, J=8.6 Hz, H-2), 1.81 (1H, m, H-3), 1.55 (1H, m, H-4b), 1.11 (1H, m, H-4a), 0.86 (3H, d, J=6.4 Hz, H-6), 0.80 (3H, t, J=7.2 Hz, H-5); $^{13}$C NMR (DMSO-d$_6$ 150 MHz): as tubulysin A (1) except Tuv δ 177.9 (s, C$_{1-4}$), 160.1 (s, C-1), 149.7 (s, C-2), 122.8 (d, C-3), 67.9 (d, C-5), 50.3 (d, C-7), 40.5 (t, C-6), 31.8 (d, C-8), 19.0 (q, C-9), 18.1 (q, C-10), Ile δ 171.4 (s, C-1), 57.1 (d, C-2), 36.2 (d, C-3), 24.6 (t, C-4), 15.6 (q, C-6), 10.4 (q, C-5); DCI MS: m/z [M+H]$^+$ 688 (100), 256 (12), 223 (6), 98 (4); HRMS (DCI): C$_{35}$H$_{54}$N$_5$O$_7$S: 688.3799 [M+H]$^+$ (calc.: 688.3744).

Methyl Ester of Tubulysin Derivative 10a:

2.5 mg (3.6 µmol) of 10a were dissolved in 200 µl of methanol; ethereal diazomethane solution was added and stirring was carried out for 10 minutes at room temperature. Purification was carried out directly by means of PLC (CH$_2$Cl$_2$/MeOH 85/15) and yielded 2.8 mg (62%) of the methyl ester of 10a.

$R_f$ (CH$_2$Cl$_2$/MeOH 85/15): 0.32; IR (KBr): $\bar{\nu}$=3380 cm$^{-1}$ (m), 2960 (s), 2931 (s), 2872 (w), 1743 (w), 1659 (vs), 1516 (m), 1371 (w), 1229 (s), 1092 (w); UV (MeOH): $\lambda_{max}$ (lg ε)=204 nm (4.53), 226 (4.27), 244 (sh, 4.01), 276 (sh, 3.38); DCI MS (120 eV, NH$_3$): 702 [M+H]$^+$; $^1$H NMR (CD$_3$OD, 300 MHz): δ=1.18 (d, 3H, Tut10-H), 3.64 (s, 3H, Tut 11-H).

Cyclotubulysin A (11a): $R^1$=OH (Scheme 1)

1 ml of 0.5 M hydrochloric acid solution was added to 9.6 mg (11.3 µmol) of tubulysin A (1) (distributed as a thin film on the glass walls of the reaction vessel) and stirring was carried out for 30 minutes at 100° C. The reaction mixture was then lyophilised and the residue was purified by means of PLC (CH$_2$Cl$_2$/MeOH 90/10), whereupon 3.9 mg (50%) of 11a and 1.6 mg (21%) of 10a were obtained.

11a:

ESI MS (1 eV): 699 [M+H]$^+$; $^1$H NMR (DMSO-d$_6$, 300 MHz): δ=8.15 (s, 1H, Tuvt3-H), 5.32 (d, 1H, Tuv5-H), 1.7 (m, 1H, Tuv6a-H), 2.3 (m, 1H, Tuv6b-H), 4.32 (m, 1H, Tuv7-H), 1.8 (m, 1H, Tuv8-H), 0.75 (d, 3H, Tuv9-H$_3$), 0.95 (d, 3H, Tuv10-H$_3$), 4.86 (d, 1H, Tuv11a-H), 5.65 (d, 1H, Tuv11b-H).

Tubulysin Derivatives 12 and 13

A tubulysin derivative 12 can be prepared from a tubulysin derivative 7a by reacting 7a with acetyl chloride in triethylamine.

By starting from a tubulysin derivative of type 7 wherein T=$OR^4$, $R^4$=$COR^5$ and $R^5$=methyl or ethyl, the resulting tubulysin derivative of type 12 can be hydrolysed, using ammonia, to form a tubulysin derivative of type 13.

Tubulysin A Methyl Ether (14a): $R^1$=OH (Scheme 3)

500 µl of absolute ethanol and 1 mg (5.3 µmol) of p-toluenesulfonic acid were added to a solution of 10.0 mg (11.9 µmol) of tubulysin A (1) in 500 µl of absolute THF. The reaction mixture was stirred for 20 minutes at 80° C. The solvent was then removed and the crude product was purified by means of PLC ($CH_2Cl_2$/MeOH 90/10). 3.1 mg (33%) of 14a were obtained.

ESI MS (1 eV): 788 [M+H]$^+$

Tubulysin Derivative 15

A tubulysin derivative 15 can be prepared by reducing a tubulysin derivative 7a using $NaCNBH_3$ and TFA in methanol.

Tubulysin Derivative 16

A tubulysin derivative 16 can be prepared by acetylating a tubulysin derivative 9a using acetyl chloride in triethylamine.

Tubulysin Derivative 17

A tubulysin derivative 17 can be prepared by catalytically hydrogenating a tubulysin derivative 9a in the presence of $CH_3COOH$/DAST using a Pd/C catalyst and elemental hydrogen.

Tubulysin Derivatives 18 and 19

A tubulysin derivative 18 can be prepared by oxidising a tubulysin derivative 9a in the presence of TPAP and NMO.

The tubulysin derivative 18 obtained can be reacted with ethylmagnesium bromide to form a tubulysin derivative 19.

Tubulysin A Methyl Ester (20a): $R^2$=$CH_3$ (scheme 6)

19.0 mg (22.5 µmol) of tubulysin A (1) were dissolved in 300 µl of methanol, and ethereal diazomethane solution was added at room temperature on two occasions spaced 15 minutes apart. The reaction mixture was concentrated and purification of the crude product was carried out by means of PLC ($CH_2Cl_2$/MeOH 90/10), whereupon 11.7 mg (61%) of 20a were obtained.

IR (KBr): $\tilde{v}$=3383 cm$^{-1}$ (m), 2962 (s), 2875 (w), 1739 (vs), 1666 (vs), 1516 (s), 1227 (vs), 1091 (w); UV (MeOH): $\lambda_{max}$ (lg $\epsilon$)=203 nm (4.61), 225 (4.34), 243 (sh, 4.11), 276 (sh, 3.41); DCI MS (120 eV, isobutane): 858 [M+H$^+$]; $^1$H NMR (DMSO-$d_6$, 300 MHz): δ=2.43 (m, 1H, Tut2-H), 1.06 (d, 3H, Tut10-H), 3.53 (s, 3H, Tut11-H); $^{13}$C NMR (DMSO-$d_6$, 75 MHz): δ=175.8 (TutC1), 35.8 (TutC2), 17.6 (TutC10), 51.3 (TutC11).

Tubulysin A Ethyl Ester (20b): $R^1$=OH, $R^2$=$C_2H_5$ (Scheme 6)

To a solution of 5.2 mg (6.2 µmol) of tubulysin A (1) in 300 µl of dichloromethane there were added 13.5 µl (9.3 µmol) of ethanol, 1.8 mg (9.3 µmol) of EDC and 57 µl (9.3 µmol) of DMAP solution (5 mg/250 µl of $CH_2Cl_2$). The reaction mixture was stirred overnight at room temperature. Purification of the crude product was then carried out by means of PLC ($CH_2Cl_2$/MeOH 90/10), whereupon 1.7 mg (32%) of 20b, 0.7 mg (13%) of 25a and 1.0 mg (18%) of 20b wherein $R^1$=OCOCH$_3$ were obtained.

20b:

DCI MS (120 eV, NH$_3$): 872 [M+H]$^+$; HRMS (DCI): $C_{45}H_{69}N_5O_{10}S$: [M+H]$^+$ calc.: 872.4843 (found: 872.4917): $^1$H NMR (CD$_3$OD, 300 MHz): δ=2.58 (m, 1H, Tut2-H, 1.19 (d, 3H, Tut10-H), 4.11 (q, 2H, Tut11-H), 1.23 (t, 3H, Tut12-H).

20b wherein $R^1$=OCOCH$_3$

R$_f$(CH$_2$Cl$_2$/MeOH 90/10): 0.51; IR (KBr): $\tilde{\mu}$=3392 cm$^{-1}$ (m), 2962 (s), 2920 (s), 2874 (w), 1736 (s), 1667 (vs), 1507 (m), 1370 (w), 1218 (s), 1195 (s); UV (MeOH): $\lambda_{max}$ (lg $\epsilon$)=203 nm (4.60), 218 (4.30), 227 (sh, 4.23), 248 (sh, 3.98); DCI MS (120 eV, NH$_3$): 914 [M+H$^+$]; HRMS (DCI): $C_{47}H_{71}N_5O_{11}S$: [M+H]$^+$ calc.: 814.4949 found: 914.5044; $^1$H NMR (CD$_3$OD, 300 MHz): δ=7.29 (d, 2H, Tut7-H), 7.02 (d, 2H, Tut8-H), 1.20 (d, 3H, Tut10-H), 4.11 (q, 2H, Tut11-H), 1.23 (t, 3H, Tut12-H), 2.28 (s, 3-H, Tut13-H).

Tubulysin A Propyl Ester (20c): $R^1$=OH, $R^2$=$C_3H_7$ (Scheme 6)

To a solution of 11.3 mg (13.4 µmol) of tubulysin A (1) in 450 µl of dichloromethane/diethyl ether (1/2) there were added 6.5 µl (67.0 µmol) of propyl iodide and 6.2 mg (26.8 µmol) of silver(I) oxide. The reaction mixture was stirred overnight at room temperature and then filtered over Celite, and the residue was washed with dichloromethane. The combined organic phases were concentrated and purified by means of PLC (CH$_2$Cl$_2$/MeOH 90/10), whereupon 7.6 mg (64%) of 20c were obtained.

IR (KBr): $\tilde{v}$=3387 cm$^{-1}$ (m), 2964 (s), 2938 (m), 2876 (w), 1737 (s), 1667 (vs), 1516 (s), 1416 (m), 1370 (w), 1225 (s), 1094 (w); UV (MeOH): $\lambda_{max}$ (lg $\epsilon$)=204 nm (4.64), 224 (4.39), 246 (sh, 4.12), 276 (3.60); DCI MS (120 eV, NH$_3$): 886 [M+H$^+$]; $^1$H NMR (CD$_3$OD, 300 MHz): δ=2.63 (m, 1H$_i$ Tut2-H), 1.68 (m, 1H, Tut3a-H), 2.03 (m, 1H$_i$ Tut3b-H), 4.32 (m, 2H, Tut4-H), 2.83 (m, 2H, Tut5-H), 6.72 (d, 1H, Tut7-H), 7.08 (d, 1H, Tut8-H), 1.20 (d, 3H, Tut10-H), 4.02 (t, 2H, Tut11-H), 1.64 (m, 2H, Tut12-H), 0.95 (t, 3H, Tut13-H); $^{13}$C NMR (CD$_3$OD, 75 MHz): δ=177.9 (TutC1), 38.1 (TutC2), 38.9 (TutC3), 50.7 (TutC$_{1-4}$), 41.5 (TutC5), 130.0 (TutC6), 116.2 (TutC7), 131.4 (TutC8), 157.1 (TutC9), 18.4 (TutC10), 67.2 (TutC11), 23.0 (TutC12), 10.7 (TutC13).

Tubulysin A Propylamide (21a): $R^1$=OH, $R^2$=$C_3H_7$ (Scheme 6)

To a solution of 4.9 mg (5.8 µmol) of tubulysin A (1) in 300 µl of dichloromethane there were added 180 µl (19.2 µmol) of EDC solution (4 mg/200 µl of CH$_2$Cl$_2$) and 36 µl (43.5 µmol) of propylamine solution (10 µl/100 µl of CH$_2$Cl$_2$). The reaction mixture was stirred for two days at room temperature. Purification was carried out by means of PLC (CH$_2$Cl$_2$/MeOH 90/10) and yielded 1.0 mg (20%) of 21a.

ESI MS (1 eV): 885 [M+H$^+$]; $^1$H NMR (CD$_3$OD, 300 MHz): δ=2.49 (m, 1H, Tut2-H), 1.14 (d 3H, Tut10-H), 3.15 (t, 2H, Tut11-H), 1.56 (m, 2H, Tut12-H), 0.96 (t, 3H, Tut13-H).

Tubulysin A Hexylamide (21b): $R^1$=OH, $R^2$=$C_6H_{13}$ (Scheme 6)

2.8 µl (16.5 µmol) of Hünig's base were dissolved in 200 µl of absolute THF at 0° C. and 1.4 µl (11.0 µmol) of isobutyl chloroformate were added. After 5 minutes, 9.3 mg (11.0 µmol) of tubulysin A (1) dissolved in 300 µl of absolute THF were added and stirred for a further 40 minutes at 0° C. 1.6 µl (12.1 µmol) of hexylamine and 2.8 µl (16.5 µmol) of Hünig's base were then added to the reaction mixture and stirring was carried out overnight at room temperature. Purification of the crude product was carried out directly by means of PLC (CH$_2$Cl$_2$/MeOH 90/10) and yielded, in addition to 6.0 mg (65%) of 1, 3.6 mg (35%) of 21b.

R$_f$ (CH$_2$Cl$_2$/MeOH 90/10): 0.41; IR (KBr): $\tilde{v}$=3389 cm$^{-1}$ (m), 2960 (s), 2932 (s), 2872 (w), 1743 (m), 1654 (vs), 1516 (m), 1418 (m), 1228 (s); UV (MeOH): $\lambda_{max}$ (lg $\epsilon$)=204 nm (4.62), 226 (4.31), 242 (sh, 4.09), 278 (sh, 3.41); DCI MS (120 eV, NH$_3$): 927 [M+H$^+$]; HRMS (DCI): C$_{49}$H$_{78}$N$_6$O$_9$S: [M+H]$^+$ calc.: 927.5629 (found: 927.5641).

Tubulysin A Benzylamide (21c): R$^1$=OH, R$^2$=CH$_2$C$_6$H$_5$ (Scheme 6)

4.5 µl (26.8 µmol) of Hünig's base were dissolved in 200 µl of absolute THF and cooled to 0° C. 2.4 µl (17.9 µmol) of chloroformic acid isobutyl ester were added to the solution and stirring was carried out for 5 minutes. Then, a solution of 10 mg (11.9 µmol) of tubulysin A in 300 µl of absolute THF was added and stirring was carried out at 0° C. After 30 minutes, 1.4 µl (13.1 µmol) of benzylamine and 3 µl (17.9 µmol) of Hünig's base were added and the reaction mixture was stirred overnight at room temperature. The reaction mixture was purified directly by means of PLC (CH$_2$Cl$_2$/MeOH 90/10), whereupon 3.5 mg (37%) of NT19 were obtained.

R$_f$ (CH$_2$Cl$_2$/MeOH 90/10): 0.40; optical rotation: [α]$^{20}$$_D$=+27.2 (c 0.22, methanol); IR (KBr): $\tilde{v}$=3383 cm$^{-1}$ (m), 2962 (m), 2935 (m), 2875 (w), 1742 (m), 1661 (vs), 1516 (m), 1420 (w), 1371 (w), 1227 (s), 1094 (w); UV (MeOH): $\lambda_{max}$ (lg $\epsilon$)=204 nm (4.62), 224 (sh, 4.24) 246 (sh, 3.94), 277 (sh, 3.24); DCI MS (120 eV, NH$_3$): [M+H$^+$]; ESI MS (1 eV): 932 [M+H]$^+$; $^1$H NMR (CD$_3$OD, 300 MHz): δ=2.54 (m, 1H, Tut2-H), 1.64 (m, 1H, Tut3a-H), 2.03 (m, 1H, Tut3b-H), 4.24 (m, 1H, Tut4-H), 2.82 (bd, 2H, Tut5-H), 7.01 (d, 2H, Tut7-H), 6.69 (d, 2H, Tut8-H), 1.17 (d, 3H, Tut10-H), 4.42 (dd, 2H, Tut11-H), 7.2-7.4 (m, 5H, Tut13, 14, 15-H); $^{13}$C NMR (CD$_3$OD, 75 MHz): δ=187.5 (TutC1), 39.1 (TutC2), 40.3 (TutC3), 51.3 (TutC4), 41.3 (TutC5), 130.0 (TutC6), 131.4 (TutC7), 116.2 (TutC8), 157.0 (TutC9), 19.1 (TutC10), 44.2 (TutC11), 140.2 (TutC12), 128.7 (TutC13), 129.5 (TutC4), 128.1 (TutC15).

Tubulysin Derivative 22

A tubulysin derivative 22 can be obtained by reducing tubulysin 1 using methyl- or ethyl-lithium to form the secondary amine.

Tubulysin Derivative 23

A tubulysin derivative 23 can be obtained by amidating tubulysin 1 in the presence of EDC in methylene chloride using 1-(2-aminoethyl)-pyrrole-2,5-dione.

Tubulysin Derivative 24

A tubulysin derivative 24 wherein T=OR$^4$, R$^4$=SO$_3$R$^6$ and R$^6$=H can be obtained by reacting tubulysin 1 with pyridine-SO$_3$. Analogously, tubulysin 1 can be reacted with phosphoric acid dimethyl ester in the presence of iodine and pyridine in methylene chloride.

Acetyl-tubulysin A (25a): R=iso-C$_4$H$_9$, R$^1$=CH$_3$ (Scheme 7)

8.9 mg of tubulysin A (1) were dissolved in 200 µl of absolute THF, and 8.2 µl (30.6 µmol) of acetyl chloride and 7.1 µmol) of triethylamine were added. The reaction mixture was stirred for 15 minutes at room temperature, 1 ml of water was then added and extraction with ethyl acetate was carried out three times. The combined organic phases were concentrated and dried under a high vacuum. The crude product was purified by means of PLC (CH$_2$Cl$_2$/MeOH 90/10), whereupon 5.6 mg (62%) of 25a were obtained.

DCI MS (120 eV, NH$_3$): 886 [M+H$^+$]; HRMS (DCI): C$_{45}$H$_{67}$N$_5$O$_{11}$S: [M+H]$^+$ calc.: 886.4636 (found: 886.4701); $^1$H NMR (CD$_3$OD, 300 MHz): δ=2.58 (m, 1H, Tut2-H), 1.73 (m, 1H, Tut3a-H), 2.06 (m, 1H, Tut3b-H), 4.39 (m, 1H, Tut4-H), 2.98 (bd, 2H, Tut5-H), 7.29 (d, 1H, Tut7-H), 7.00 (d, 1H, Tut8-H), 1.21 (d, 3H, Tut10-H), 2.27 (s, 3H, Tut12-H); $^{13}$C NMR (CD$_3$OD, 75 MHz): δ=181.1 (TutC1), 38.7 (TutC2), 39.4 (TutC3), 51.1 (TutC4), 41.2 (TutC5), 137.2 (TutC6), 131.4 (TutC7), 122.5 (TutC8), 150.8 (TutC9), 18.8 (TutC10), 171.2 (TutC11), 20.9 (TutC12).

Isobutyryl-tubulysin A (25b): R=iso-C$_4$H$_9$, R$^1$=CH(CH$_3$)$_2$ (Scheme 7)

15.1 mg (17.8 µmol) of tubulysin A (1) were dissolved in 400 µl of absolute THF, and 5.6 µl (53.4 µmol) of isobutyric acid chloride and 12.5 µl (89.0 µmol) of triethylamine were added. The reaction mixture was stirred for 30 minutes at room temperature, 2 ml of water were then added and extraction with ethyl acetate was carried out three times. The combined organic phases were dried over sodium sulfate and concentrated. Purification of the crude product was carried out by means of PLC (CH$_2$Cl$_2$/MeOH 90/10) and yielded 5.3 mg (32%) of NT20.

R$_f$ (CH$_2$Cl$_2$/MeOH 90/10): 0.36; optical rotation: [α]$^{20}$$_D$=+11.5 (c 0.35, methanol); IR (KBr): $\tilde{v}$=3392 cm$^{-1}$ (m), 2964 (m), 2936 (m), 2875 (w), 1755 (s), 1668 (vs), 1544 (w), 1508 (w), 1468 (w), 1420 (w), 1371 (w), 1227 (s), 1167 (w); UV (MeOH): $\lambda_{max}$ (lg $\epsilon$)=204 nm (4.54), 223 (sh, 4.20); DCI MS (120 eV, NH$_3$): [M+H$^+$]; ESI MS (1 eV): 913 [M+H)+; $^1$H NMR (CD$_3$OD, 300 MHz): δ=2.59 (m, 1H, Tut2-H), 1.73 (m, 1H, Tut3a-H), 2.07 (m, 1H, Tut3b-H), 4.39 (m, 1H, Tut4-H), 2.98 (bd, 2H, Tut5-H), 6.99 (d, 2H, Tut7-H), 7.30 (d, 2H, Tut8-H), 1.22 (d, 3H, Tut10-H), 2.82 (d, 1H, Tut12-H), 1.31 (d, 6H, Tut13, 14-H); $^{13}$C NMR (CD$_3$OD, 75 MHz): δ=181.1 (TutC1), 38.7 (TutC2), 39.4 (TutC3), 51.1 (TutC4), 41.2 (TutC5), 137.2 (TutC6), 131.4 (TutC7), 122.3 (TutC8), 150.8 (TutC9), 18.8 (TutC10), 177.2 (TutC11), 35.3 (TutC12), 19.2 (TutC13, 14).

Tubulysin A Allyl Ether Allyl Ester (26a): R=Iso-C$_4$H$_9$, R$^1$=CH$_2$CHCH$_2$ (Scheme 7)

To 6.0 mg (7.1 µmol) of tubulysin A (1), dissolved in 300 µl of dichloromethane/diethyl ether (1/1), there were added 6.2 µl (71.2 µmol) of allyl bromide and 6.6 mg (28.5 µmol) of silver(I) oxide and stirring was carried out overnight at room temperature. Filtration over Celite was then performed. The residue was washed with dichloromethane and the combined organic phases were concentrated. Purification of the crude product was carried out by means of PLC (CH$_2$Cl$_2$/MeOH 90/10) and yielded 2.9 mg (44%) of 26a.

ESI MS (1 eV): 924 [M+H)$^+$; $^1$H NMR (CD$_3$OD, 400 MHz): δ=7.17 (d, 2H, Tut7-H), 6.86 (d, 2H, Tut8-H), 1.22 (d, 3H, Tut10-H), 4.5-4.6 (m, 4H, Tut11-H, Tut14-H), 5.93 (m, 1H, Tut12-H), 5.1-5.5 (m, 4H, Tut13-H, Tut16-H), 6.07 (m, 1H, Tut15-H).

Tubulysin A Methyl Ether Methyl Ester (26b): R=Iso-C$_4$H$_9$, R$^1$=CH$_3$ (Scheme 7)

21.7 mg (25.7 µmol) of tubulysin A (1) were dissolved in 200 µl of methanol; ethereal diazomethane solution was added at room temperature on three occasions spaced 15 minutes apart and stirring was carried out overnight. The reaction mixture was then dried. Purification was carried out by means of PLC (CH$_2$Cl$_2$/MeOH 90/10) and yielded 10.3 mg (46%) of 26 and 5.0 mg (23%) of tubulysin A methyl ester (20a).

DCI MS (120 eV, NH$_3$): 872 [M+H$^+$]; HRMS (DCI): C$_{45}$H$_{69}$N$_5$O$_{10}$S: [M+H]$^+$ calc.: 872.4843 (found: 872.4818);

¹H NMR (CD₃OD, 400 MHz): δ=2.6 (m, 1H, Tut2-H), 2.86 (d, 2H, Tut5-H), 7.17 (d, 2H, Tut7-H), 6.85 (d, 2H, Tut8-H), 1.19 (d, 3H, Tut10-H), 3.65 (s, 3H, Tut11-H), 3.78 (s, 3H, Tut12-H)

Tubulysin A Methyl Ether (27a): R=iso-C₄H₉, R¹=CH₃ (Scheme 7)

1.6 mg (1.8 µmol) of 26a (R¹=CH₃) were dissolved in 50 µl of DMSO, and 700 µl of phosphate buffer (20 mM KH₂PO₄, pH=7.3) were added. The reaction batch was placed for 5 minutes in an ultrasonic bath, 72 µl of pig liver esterase (Boehringer-Mannheim) were then added and stirring was carried out for 4 hours at 36° C. For isolation of the product, extraction was carried out with ethyl acetate three times, and the combined organic phases were dried. Purification of the crude product was carried out by means of PLC (CH₂Cl₂/MeOH 90/10) and yielded 0.5 mg (32%) of 27a.

DCI MS (120 eV, NH₃): 858 [M+H⁺]; HRMS (DCI): C₄₄H₅₇N₅O₁₀S: [M+H]⁺ calc.: 857.4687 (found: 858.4740); ¹H NMR (CD₃OD, 300 MHz): δ=2.8 (m, 2H, Tut5-H), 7.19 (d, 2H, Tut7-H), 6.84 (d, 2H, Tut8-H), 3.78 (s, 3H, Tut11-H).

Iodination of Tubulysin A (28a, 29a): R=Iso-C₄H₉, Hal=I (Scheme 8)

11.0 mg (13.1 µmol) of tubulysin A (1) were dissolved in 200 µl of methanol, and 13.0 µl of iodine monochloride solution (13.1 µmol) were added. The reaction mixture was stirred for 15 minutes at room temperature and then purified directly by means of PLC (CH₂Cl₂/MeOH 90/10). 3.1 mg (25%) of 28a and 3.9 mg (27%) of 29a were obtained in the process.

28a:
ESI MS (1 eV): 970 [M+H]⁺; ¹H NMR (CD₃OD, 300 MHz): δ=2.58 (m, 1H, Tut2-H), 1.71 (m, 1-H, Tut3a-H), 2.05 (m, 1-H, Tut3b-H), 4.28 (m, 1-H, Tut4-H), 2.82 (m, 2H, Tut5-H), 7.10 (dd, 2H, Tut7-H), 6.75 (d, 2H, Tut8-H), 7.55 (d, 1H, Tut12-H); ¹³C NMR (CD₃OD, 75 MHz): δ=181.2 (TutC1), 38.7 (TutC2), 39.5 (TutC3), 51.4 (TutC4), 40.6 (TutC5), 132.6 (TutC6), 131.5 (TutC7), 115.6 (TutC8), 156.5 (TutC9), 18.8 (TutC10), 84.4 (TutC11), 141.2 (TutC12).

29a:
ESI MS (1 eV): 1096 [M+H]⁺; ¹H NMR (CD₃OD, 600 MHz): δ=2.58 (m, 1H, Tut2-H), 1.73 (m, 1H, Tut3a-H), 2.05 (m, 1H, Tut3b-H), 4.25 (m, 1H, Tut4-H), 2.75 (dd, 1H, Tut5a-H), 2.86 (dd, 1H, Tut5b-H), 7.61 (s, 2H, Tut7, 12-H); ¹³C NMR (CD₃OD, 75 MHz): δ=181.1 (TutC1), 38.6 (TutC2), 39.6 (TutC3), 51.5 (TutC4), 40.1 (TutC5), 135.8 (TutC6), 141.5 (TutC7, 12), 85.1 (TutC8, 11), 155.2 (TutC9), 18.8 (TutC10).

Nitrotubulysin A (30a): R=iso-C₄H₉ (Scheme 8)

To a solution of 12.5 mg (14.8 µmol) of tubulysin A (1) in 400 µl of ethanol there were added 100 µl of glacial acetic acid and 20.5 mg (296.6 µmol) of sodium nitrite, dissolved in 100 µl of water. The reaction mixture was stirred for two days at room temperature and was then dried under a high vacuum. The crude product was purified by means of PLC (CH₂Cl₂/MeOH 90/10), whereupon 9.8 mg (74%) of 30 were obtained.

IR (KBr): ṽ=3411 cm⁻¹ (m), 2962 (m), 2932 (m), 2873 (w), 1741 (s), 1666 (vs), 1539 (s), 1492 (w), 1424 (w), 1370 (w), 1223 (s); UV (MeOH): λ$_{max}$ (lg ε)=205 nm (4.56), 216 (sh, 4.42), 234 (sh, 4.19), 274 (3.77), 360 (3.43); DCI MS (120 eV, NH₃): 889 [M+H⁺]; ¹H NMR (CD₃OD, 400 MHz): δ=2.60 (m, 1H, Tut2-H), 1.74 (m, 1H, Tut3a-H), 2.09 (m, 1H, Tut3b-H), 4.37 (ddd, 2H, Tut4-H), 2.91 (dd, 1H, Tut5a-H), 3.01 (dd, 1H, Tut5b-H), 7.56 (dd, 1H, Tut7-H), 7.07 (d, 1H, Tut8-H), 1.27 (d, 3H, Tut10-H), 7.97 (d, 1H, Tut12-H); ¹³C NMR (CD₃OD, 400 MHz): δ=180.7 (TutC1), 38.5 (TutC2), 39.6 (TutC3), 51.0 (TutC4), 40.7 (TutC5), 132.0 (TutC6), 139.4 (TutC7), 120.8 (TutC8), 154.2 (TutC9), 18.8 (TutC10), 135.3 (TutC11), 126.5 (TutC12).

Tubulysin Derivatives 31 and 32

A tubulysin derivative 31 can be obtained by catalytically reducing nitro-tubulysin A (30a) in ethanol using elemental hydrogen together with a Pd/C catalyst.

The tubulysin derivative 31 obtained can be acylated to form a tubulysin derivative 32 using acetic anhydride.

Tubulysin A N-oxide (33a): R=iso-C₄H₉ (Scheme 9)

9.9 mg (11.7 µmol) of tubulysin A (1) were dissolved in 200 µl of dichloromethane; 290 µl (11.7 µmol) of m-CPBA solution (10 mg/ml of dichloromethane) were added and stirring was carried out at room temperature for 30 minutes. After the reaction mixture was reduced, purification was carried out directly by means of PLC (CH₂Cl₂ methanol 85/15), whereupon 5.2 mg (52%) of 33a were obtained.

ESI MS (1 eV): 860 [M+H]⁺.

Tubulysin Derivative 34

A tubulysin derivative 34 can be obtained by treating tubulysin A N-oxide (33a) with acetic anhydride at about 75° C.

ABBREVIATIONS

| Abbreviation | Name |
| --- | --- |
| C₅Cl₅NF-triflate | N-fluoropentachloropyridinium triflate |
| CH₃CN | acetonitrile |
| DAST | (diethylamino)sulfur trifluoride |
| DMAP | dimethylaminopyridine |
| EDC | N-ethyl-N'-(3-dimethylaminopropyl)-carbodiimide |
| ICl | iodine monochloride |
| m-CPBA | meta-chloroperbenzoic acid |
| Me₃SiCl | trimethylchlorosilane |
| NaCNBH₃ | sodium cyanoborohydride |
| NBS | N-bromosuccinimide |
| NMO | N-methyl-morpholine N-oxide |
| p-CH₃—C₆H₄SO₂OH | para-toluenesulfonic acid |
| TFA | trifluoroacetic acid |
| THF | tetrahydrofuran |
| TPAP | tetra-propylammonium perruthenate |

The invention claimed is:
1. A compound of formula I (tubulysin):

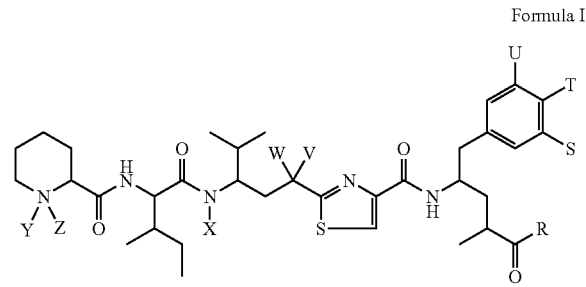

Formula I wherein R, R¹, R⁴, R⁵, R⁶, R⁷, R⁸, R⁹, R¹⁰, R¹¹, S, T, U, V, W, X, Y and Z have the following meanings:
R=OR¹
R¹=alkyl or aryl
S=H
U=H T=H or OR$^4$
R$^4$=H, alkyl, aryl, COR$^5$, P(O)(OR$^6$)$_2$ or SO$_3$R$^6$
R$^5$=alkyl, alkenyl, or aryl
R$^6$=H, alkyl or a metal ion
V=OR$^7$
R$^7$=COR$^8$
R$^8$=alkyl, alkenyl or aryl
W=H
X=H, alkyl, alkenyl or CH$_2$OR$^9$
R$^9$=H, alkyl, alkenyl, aryl or COR$^{10}$
R$^{10}$=alkyl, alkenyl, or aryl
Y=free electron pair
R$^{11}$=alkyl, CF$_3$ or aryl and/or
Z=CH$_3$ or COR$^{11}$.

2. The compound according to claim 1, wherein
R, R$^1$, R$^4$, R$^5$, R$^8$, R$^9$, R$^{10}$ and/or R$^{11}$=unsubstituted or substituted phenyl,
R$^5$=C$_{1-4}$alkyl or C$_{2-6}$alkenyl
R$^5$ and/or X=C$_{2-4}$alkenyl
R$^6$=an alkali metal ion or an alkaline earth metal ion
R$^8$ and/or R$^9$=C$_{2-4}$alkenyl and/or
R$^{10}$=C$_{2-6}$alkenyl.

3. The compound according to claim 1, wherein alkyl is branched, unbranched or cyclic C$_{1-20}$alkyl.

4. The compound according to claim 1, wherein alkenyl is branched, unbranched or cyclic C$_{2-20}$alkenyl.

5. The compound according to claim 1, wherein aryl is phenyl, naphthyl and biphenylyl.

6. The compound according to claim 1, wherein alkyl, alkenyl, and aryl are unsubstituted or substituted.

7. The compound according to claim 2, wherein R, R$^1$, R$^4$, R$^5$, R$^8$, R$^9$, R$^{10}$ and/or R$^{11}$=C$_{1-4}$ alkyl-substituted phenyl.

8. The compound according to claim 2, wherein R$^6$=an Na ion.

9. The compound according to claim 2, wherein R$^{10}$=C$_{2-4}$ alkenyl.

10. The compound according to claim 3, wherein the alkyl is cyclic C$_{1-7}$alkyl or C$_{1-8}$alkyl.

11. The compound according to claim 10, wherein the alkyl is cyclic C$_{1-4}$alkyl.

12. The compound according to claim 11, wherein the alkyl is selected from the group consisting of methyl, ethyl, propyl, isopropyl, n-butyl, isobutyl, sec-butyl, tert-butyl, and cycloalkyl having from 3 to 8 carbon atoms in the ring.

13. The compound according to claim 4, wherein the alkenyl is C$_{2-7}$alkenyl or C$_{2-6}$alkenyl.

14. The compound according to claim 13, wherein the alkenyl is C$_{2-4}$alkenyl.

15. The compound according to claim 14, wherein the alkenyl is selected from the group consisting of vinyl, allyl propen-1-yl, propen-2-yl, but-1-en-1-yl, but-1-en-2-yl, but-1-en-3-yl, but-1-en-4-yl, but-2-en-1-yl, but-2-en-2-yl, 2methyl-propen-1-yl, 2-methyl-propen-3-yl, and cycloalkenyl having from 3 to 8 carbon atoms in the ring and the number of double bonds in the alkenyl groups being from 1 to 3.

16. The compound according to claim 6, wherein the alkyl, alkenyl, and aryl carry, in any position, from 1 to 3 substituents from the group formed by C$_{1-3}$alkyl, C$_{1-3}$alkoxy, hydroxy, amino (NH$_2$) and nitro (NO$_2$).

* * * * *